US008426614B2

(12) United States Patent
Arai et al.

(10) Patent No.: US 8,426,614 B2
(45) Date of Patent: Apr. 23, 2013

(54) EPOXY COMPOUND AND PROCESS FOR PRODUCING THE EPOXY COMPOUND

(75) Inventors: Yoshikazu Arai, Minato-ku (JP); Hiroshi Uchida, Minato-ku (KR)

(73) Assignee: Showa Denko K.K., Tokyo (JP)

( * ) Notice: Subject to any disclaimer, the term of this patent is extended or adjusted under 35 U.S.C. 154(b) by 303 days.

(21) Appl. No.: 12/933,828

(22) PCT Filed: Mar. 23, 2009

(86) PCT No.: PCT/JP2009/055576
§ 371 (c)(1),
(2), (4) Date: Sep. 21, 2010

(87) PCT Pub. No.: WO2009/119469
PCT Pub. Date: Oct. 1, 2009

(65) Prior Publication Data
US 2011/0021788 A1    Jan. 27, 2011

(30) Foreign Application Priority Data
Mar. 24, 2008 (JP) .................... 2008-075344

(51) Int. Cl.
C07F 7/02 (2006.01)
C07F 7/08 (2006.01)
C08L 83/04 (2006.01)

(52) U.S. Cl.
USPC .............. 549/215; 528/31; 525/479

(58) Field of Classification Search .......... None
See application file for complete search history.

(56) References Cited

U.S. PATENT DOCUMENTS

| 5,206,328 A |   | 4/1993  | Okamura et al. |
|-------------|---|---------|----------------|
| 5,468,826 A | * | 11/1995 | Gentle et al. .................... 528/15 |
| 5,484,867 A |   | 1/1996  | Lichtenhan et al. |
| 5,484,950 A | * | 1/1996  | Crivello ........................ 549/215 |
| 5,516,823 A | * | 5/1996  | Gentle et al. ................. 524/264 |
| 5,863,970 A | * | 1/1999  | Ghoshal et al. ............... 523/434 |
| 6,129,955 A |   | 10/2000 | Papathomas |

(Continued)

FOREIGN PATENT DOCUMENTS

EP    1 645 560 A1    4/2006
EP    2 055 708 A1    5/2009

(Continued)

OTHER PUBLICATIONS

Jiwon Choi, et al., Organic/Inorganic Hybrid Composites from Cubic Silsesquioxanes. Epoxy Resins of Octa(dimethylsiloxyethylcyclohexylepoxide) Silsesquioxane, Macromolecules, Jul. 29, 2003, pp. 5666-5682, vol. 36, No. 15.

(Continued)

Primary Examiner — Robert S Loewe
(74) Attorney, Agent, or Firm — Sughrue Mion, PLLC

(57) ABSTRACT

An object of the present invention is to provide an epoxy compound which has a quick curing rate and is excellent in an etching durability and a selectivity and which is liquid at room temperature and a process for producing the above epoxy compound. The epoxy compound of the present application is represented by Formula (I):

$$(YSiO_{3/2})_n \qquad (I)$$

(in Formula (I), p (p is a natural number equal to n or less) groups of Y out of n groups thereof represent specific groups, and (n−p) groups of Y represent a hydrogen atom or —OSiR$^1_2$H; and n represents an integer of 2 to 500).

25 Claims, 14 Drawing Sheets

U.S. PATENT DOCUMENTS

| | | | |
|---|---|---|---|
| 6,210,790 B1 * | 4/2001 | Crivello | 428/325 |
| 6,265,459 B1 | 7/2001 | Mahoney et al. | |
| 6,482,868 B1 | 11/2002 | Mahoney et al. | |
| 6,790,473 B2 | 9/2004 | Papathomas et al. | |
| 7,026,013 B2 | 4/2006 | Deruelle et al. | |
| 7,034,089 B2 * | 4/2006 | Herr et al. | 525/479 |
| 7,049,044 B2 * | 5/2006 | Gonsalves et al. | 430/270.1 |
| 7,732,552 B2 * | 6/2010 | Lejeune et al. | 528/10 |
| 7,880,018 B2 | 2/2011 | Sasaki et al. | |
| 8,138,296 B2 | 3/2012 | Sasaki et al. | |
| 2005/0042458 A1 * | 2/2005 | Ghoshal | 428/417 |
| 2005/0277058 A1 * | 12/2005 | Iwabuchi et al. | 430/270.1 |
| 2006/0074213 A1 | 4/2006 | Kiyomori et al. | |
| 2012/0215019 A1 * | 8/2012 | Arkles et al. | 556/456 |

FOREIGN PATENT DOCUMENTS

| | | |
|---|---|---|
| JP | 3-255130 A | 11/1991 |
| JP | 9-136957 A | 5/1997 |
| JP | 9-165436 A | 6/1997 |
| JP | 2004502003 A | 1/2004 |
| JP | 2006-104325 A | 4/2006 |
| JP | 2008-013544 A | 1/2008 |
| WO | 2004029126 A1 | 8/2004 |
| WO | 2007/142248 A1 | 12/2007 |
| WO | 2008/020637 A1 | 2/2008 |

OTHER PUBLICATIONS

Japanese Office Action issued in corresponding Japanese Application No. 2010-505608, dated Nov. 20, 2012.

Junchao Huang et al.; Organic-inorganic nanocomposites from cubic silsesquioxane epoxides: direct characterization of interphase, and thermomechanical properties, Polymer, vol. 46, Issue 18, Aug. 23, 2005, pp. 7018-7027.

* cited by examiner

EPOXY COMPOUND AND PROCESS FOR PRODUCING THE EPOXY COMPOUND

BACKGROUND OF THE INVENTION

The present invention relates to a novel epoxy compound and a process for producing the above epoxy compound, more specifically to an epoxy compound which is useful as a sealing material and a coating material for electric, electronic and optical parts and a raw material for adhesives, coating materials, silane coupling agents, modified silicones and the like and useful as a resist in a semiconductor production process, a magnetic recording medium production process for patterned media and the like and a process for producing the above epoxy compound.

RELATED ART

Epoxy compounds provide cured products which are excellent in mechanical properties, a moisture resistance, electric properties and the like by curing with various curing agents, and therefore they are used in wide fields such as sealing materials, molding materials, cast molding materials, laminated materials, composite materials, adhesives, powder coating materials and the like for electric, electronic and optical parts. In recent years, as technologies progress, epoxy compounds have been requested to be provided with high performances regarding a curing property, a processing facility and the like. In particular, resist materials in a semiconductor production process are requested to have an etching selectivity.

It is considered, for example, to introduce a siloxane skeleton into an epoxy compound for the purpose of providing such an etching selectivity that a durability against specific gases among various etching gases is high, and organopolysiloxane and cyclic siloxane each having a 3-glycidoxypropyl group or a 2-(3,4-epoxycyclohexyl)ethyl group at an end of a molecular chain or a side chain of a molecular chain are proposed (refer to a patent document 1). However, in a case of the production process described in the above document, two steps having an epoxidation step of siloxane and a high molecular weight-providing step thereof are required, and in addition thereto, treatment of a basic catalyst is essential. Accordingly, complication on the production is involved therein.

Also, epoxy compounds having a glycidyl group require relatively longer curing time as compared with those of epoxy compounds having other curable functional groups, and therefore they are desired to be epoxy compounds having a characteristic in which they are cured in a shorter period. Further, a conventional production process for siloxane compounds having a curable functional group includes a so-called sol-gel process in which alkoxysilanes are synthesized by hydrolysis reaction, but the product obtained is a mixture, and it is difficult to control components thereof. Particularly when stored for long time, the product is likely to be gelatinized, and therefore epoxy compounds which do not bring about the above problems and a production process for the same are required.

Further, when cage-like hydrogenated silsesquioxane is subjected to hydrosilylation with 4-vinylcyclohexene oxide, the product is solid and therefore is not suited to uses such as a UV resist and the like. Accordingly, epoxy compounds which are liquid at room temperature, that is, 10 to 30° C. are desired in order to apply them to the above uses.

Patent document 1: Japanese Patent Application Laid-Open No. 255130/1991

DISCLOSURE OF THE INVENTION

An object of the present application is to provide an epoxy compound which solves the problems described above and which is excellent in a curing property and an etching selectivity. Further, an object thereof is to provide an epoxy compound which is liquid at room temperature in addition to having the characteristics described above from the viewpoint of a processing facility.

Intense investigations repeated by the present inventors in order to solve the problems described above have come to result in finding the present invention. That is, the present invention relates to the following items [1] to [15].

[1] An epoxy compound represented by Formula (I):

[Ka 1]

(in Formula (I), p (p is a natural number equal to n or less) groups of Y out of n groups thereof represent groups represented by any of Formulas (1a) to (5a) shown below, and (n−p) groups of Y represent a hydrogen atom or —OSiR$^1_2$H; n represents an integer of 2 to 500; R$^1$ described above each represents independently an alkyl group having 1 to 5 carbon atoms):

[Ka 2]

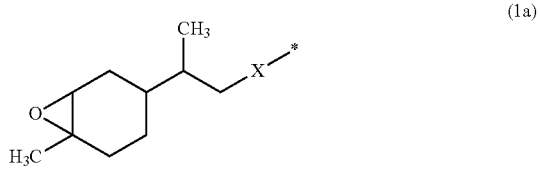

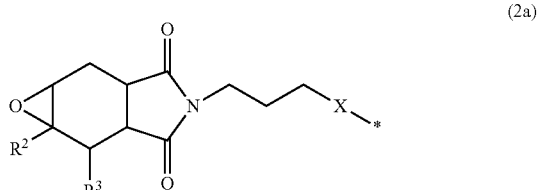

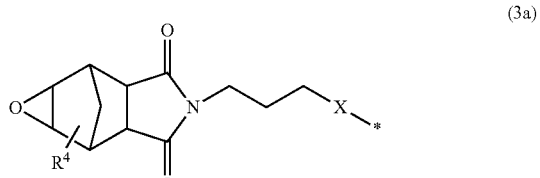

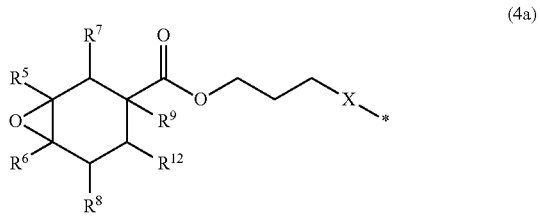

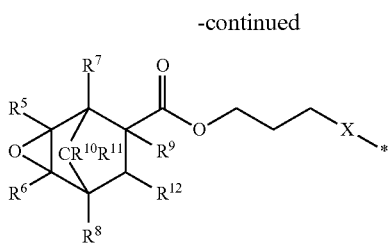

(5a)

(in Formulas (1a) to (5a), $R^2$ and $R^3$ each represent independently a hydrogen atom, an alkyl group having 1 to 6 carbon atoms or a trialkylsilyl group having 1 to 4 carbon atoms;

$R^4$ represents a hydrogen atom, an alkyl group having 1 to 6 carbon atoms or a trialkylsilyl group having 1 to 4 carbon atoms; $R^5$ to $R^{11}$ each represent independently a hydrogen atom, an alkyl group having 1 to 6 carbon atoms or a trialkylsilyl group having 1 to 4 carbon atoms;

$R^{12}$ represents a hydrogen atom, an alkyl group having 1 to 6 carbon atoms, a trialkylsilyl group having 1 to 4 carbon atoms or an aryl group;

* represents a bonding part with Si shown in Formula (I), and —X—* represents —* in which X is a single bond or a group represented by Formula (x) shown below):

[Ka 3]

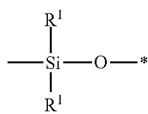

(x)

(in Formula (x), $R^1$ represents an alkyl group having 1 to 5 carbon atoms).

[2] The epoxy compound as described in the above item [1], wherein the epoxy compound is an epoxy compound having a cage-like silsesquioxane structure or a ladder-like silsesquioxane structure.

[3] The epoxy compound as described in the above item [1] or [2], wherein in Formulas (1a) to (5a), —X—* is the group represented by Formula (x) described above, and in Formula (x), $R^1$ is methyl or ethyl.

[4] The epoxy compound as described in any of the above item [1] or [3], wherein in Formulas (1a) to (5a), $R^2$ to $R^{11}$ each are independently a hydrogen atom or methyl, and $R^{12}$ is a hydrogen atom, methyl or phenyl.

[5] An epoxy compound represented by Formula (II):

[Ka 4]

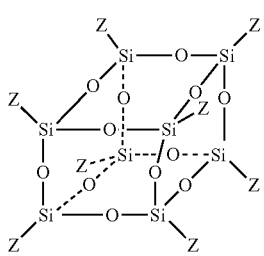

(II)

(in Formula (II), q (q is a natural number equal to 8 or less) groups out of eight Z represent —OSiR$^1_2$Y$^1$, and (8−q) groups of Z represent a hydrogen atom or —OSiR$^1_2$H; $R^1$ represents an alkyl group having 1 to 5 carbon atoms; and $Y^1$ represents a group represented by any of Formulas (1b) to (5b) shown below):

[Ka 5]

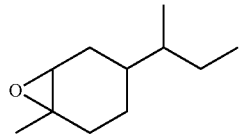

(1b)

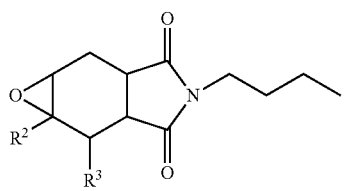

(2b)

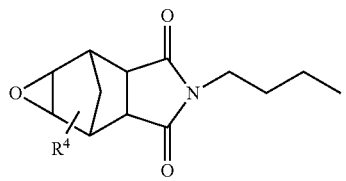

(3b)

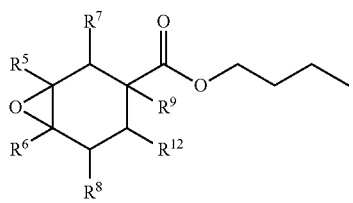

(4b)

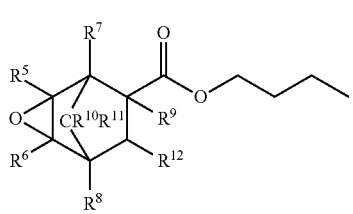

(5b)

(in Formulas (1b) to (5b), $R^2$ and $R^3$ each represent independently a hydrogen atom, an alkyl group having 1 to 6 carbon atoms or a trialkylsilyl group having 1 to 4 carbon atoms;

$R^4$ represents a hydrogen atom, an alkyl group having 1 to 6 carbon atoms or a trialkylsilyl group having 1 to 4 carbon atoms; $R^5$ to $R^{11}$ each represent independently a hydrogen atom, an alkyl group having 1 to 6 carbon atoms or a trialkylsilyl group having 1 to 4 carbon atoms;

$R^{12}$ represents a hydrogen atom, an alkyl group having 1 to 6 carbon atoms, a trialkylsilyl group having 1 to 4 carbon atoms or an aryl group).

[6] The epoxy compound as described in the above item [5], wherein in Formula (II), $R^1$ is methyl or ethyl.

[7] The epoxy compound as described in the above item [5] or [6], wherein in Formulas (1b) to (5b), $R^2$ to $R^{11}$ each are independently a hydrogen atom or methyl, and $R^{12}$ is a hydrogen atom, methyl or phenyl.

[8] The epoxy compound as described in any of the above items [1] to [7], wherein it is liquid at 10 to 30° C.

[9] A production process for the epoxy compound as described in the above item [1], comprising the step of:

reacting a polysilicone compound represented by Formula (III) or (IV):

[Ka 6]

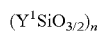
(III)

(in Formula (III), $Y^1$ represents a hydrogen atom or $—OSiR^1{}_2H$; $R^1$ represents an alkyl group having 1 to 5 carbon atoms; and n represents an integer of 2 to 500):

[Ka 7]

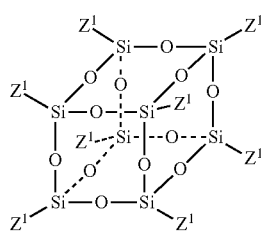
(IV)

(in Formula (IV), $Z^1$ represents $—OSiR^1{}_2H$, and $R^1$ represents an alkyl group having 1 to 5 carbon atoms) with an epoxy compound represented by any of Formulas (6) to (10) shown below:

[Ka 8]

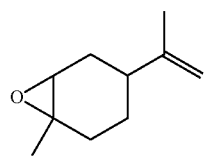
(6)

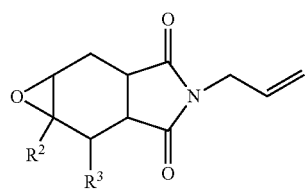
(7)

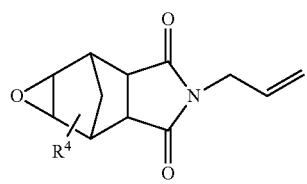
(8)

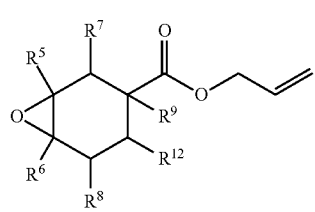
(9)

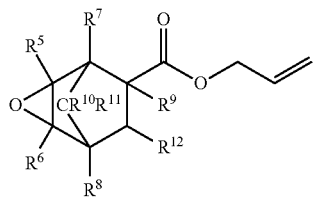
(10)

(in Formulas (6) to (10), $R^2$ and $R^3$ each represent independently a hydrogen atom, an alkyl group having 1 to 6 carbon atoms or a trialkylsilyl group having 1 to 4 carbon atoms;

$R^4$ represents a hydrogen atom, an alkyl group having 1 to 6 carbon atoms or a trialkylsilyl group having 1 to 4 carbon atoms; $R^5$ to $R^{11}$ each represent independently a hydrogen atom, an alkyl group having 1 to 6 carbon atoms or a trialkylsilyl group having 1 to 4 carbon atoms;

$R^{12}$ represents a hydrogen atom, an alkyl group having 1 to 6 carbon atoms, a trialkylsilyl group having 1 to 4 carbon atoms or an aryl group) at 10 to 200° C.

[10] The production process for the epoxy compound as described in the above item [9], wherein the polysilicone compound described above is the polysilicone compound represented by Formula (III), and the above polysilicone compound is a polysilicone compound having a cage-like silsesquioxane structure or a ladder-like silsesquioxane structure.

[11] The production process for the epoxy compound as described in the above item [9], wherein the polysilicone compound described above is the polysilicone compound represented by Formula (IV), and in Formula (IV) described above, $R^1$ is methyl or ethyl.

[12] The production process for the epoxy compound as described in any of the above items [9] to [11], wherein in Formulas (6) to (10), $R^2$ to $R^{11}$ each are independently a hydrogen atom or methyl, and $R^{12}$ is a hydrogen atom, methyl or phenyl.

[13] The production process for the epoxy compound as described in any of the above items [9] to [12], wherein the epoxy compound and the polysilicone compound are blended so that an equivalent of a —SiH group contained in the polysilicone compound is 0.3 to 1.5 based on 1 equivalent of an ethylenical double bond contained in the epoxy compound.

[14] An epoxy compound obtained by blending a polysilicone compound represented by Formula (IV):

[Ka 9]

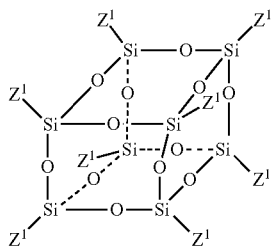
(IV)

(in Formula (IV), $Z^1$ represents $—OSiR^1{}_2H$, and $R^1$ represents an alkyl group having 1 to 5 carbon atoms) with an epoxy compound represented by any of Formulas (6) to (10) shown below:

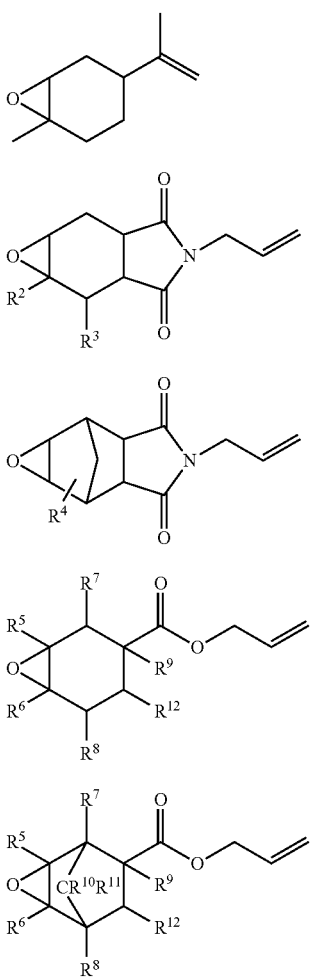

(in Formulas (6) to (10), $R^2$ and $R^3$ each represent independently a hydrogen atom, an alkyl group having 1 to 6 carbon atoms or a trialkylsilyl group having 1 to 4 carbon atoms; $R^4$ represents a hydrogen atom, an alkyl group having 1 to 6 carbon atoms or a trialkylsilyl group having 1 to 4 carbon atoms; $R^5$ to $R^{11}$ each represent independently a hydrogen atom, an alkyl group having 1 to 6 carbon atoms or a trialkylsilyl group having 1 to 4 carbon atoms;

$R^{12}$ represents a hydrogen atom, an alkyl group having 1 to 6 carbon atoms, a trialkylsilyl group having 1 to 4 carbon atoms or an aryl group) so that an equivalent of a —SiH group contained in the polysilicone compound is 0.3 to 1.5 based on 1 equivalent of an ethylenical double bond contained in the epoxy compound and subjecting them to hydrosilylation reaction at 10 to 200° C.

[15] The epoxy compound as described in the above item [14], wherein $R^1$ of the polysilicone compound represented by Formula (IV) is methyl, and the epoxy compound described above is the epoxy compound represented by Formula (6) or (9).

ADVANTAGEOUS EFFECTS OF THE INVENTION

The epoxy compound of the present invention is a so-called alicyclic epoxy compound having an alicyclic epoxy group and has a high storage stability as compared with that of an epoxy compound of a glycidyl type, and it is easily used in an industrial scale. Further, an alicyclic epoxy group contained in the epoxy compound of the present invention has a higher cationic polymerizability than a usual glycidyl group. Accordingly, the above epoxy compound is very suitable for electronic materials which are required to be cured at lower temperature for shorter time.

Accordingly, the epoxy compound of the present invention exerts an excellent etching durability as a resist used in a dry etching step in a semiconductor production process, a magnetic recording medium production process for patterned media and the like. That is, the above epoxy compound is useful in wide fields such as molding materials and sealing materials for electric, electronic and optical parts, cast molding materials, laminated materials, composite materials, adhesives, powder coating materials and the like.

A production process for the epoxy compound of the present invention comprises a step in which the specific epoxy compound is reacted with the specific polysilicone compound on prescribed conditions, and therefore the epoxy compound having a high stability as compared with that of an epoxy compound produced by a process according to a conventionally known sol-gel method can be obtained.

Also, in a production process for the epoxy compound of the present invention, a so-called alicyclic epoxy compound such as limonene oxide, allyl 3,4-epoxycyclohexane-1-carboxylate is used as the specific epoxy compound, and therefore the epoxy compound of the present invention can be obtained as a liquid. Accordingly, the above epoxy compound is suitable as well for uses such as UV nanoimprint which is required to be liquid.

BEST MODE FOR CARRYING OUT THE INVENTION

Figure 1:
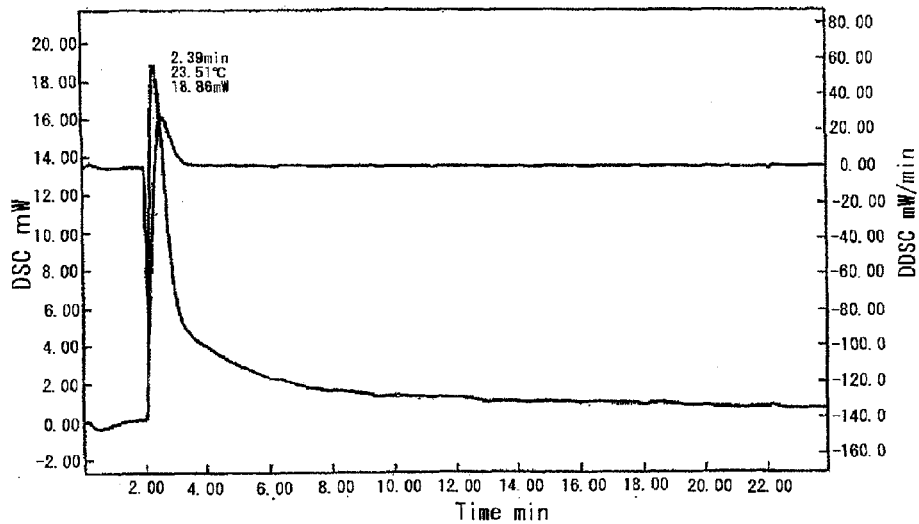
FIG. 1 is chart diagrams of DSC and DDSC of the epoxy compound (V) obtained in Example 1.

The present invention shall be explained below in detail.
<Epoxy Compound>
The epoxy compound of the present invention is characterized by being represented by Formula (I):
[Ka 11]

$$(YSiO_{3/2})_n \quad (I)$$

In Formula (I), p (p is a natural number equal to n or less) groups of Y represent groups represented by any of Formulas (1a) to (5a) shown below, and (n–p) groups of Y represent a hydrogen atom or a —OSiR$^1{}_2$H group; n represents an integer of 2 to 500, preferably an even number of 6 to 18 and more preferably 8.

[Ka 12]

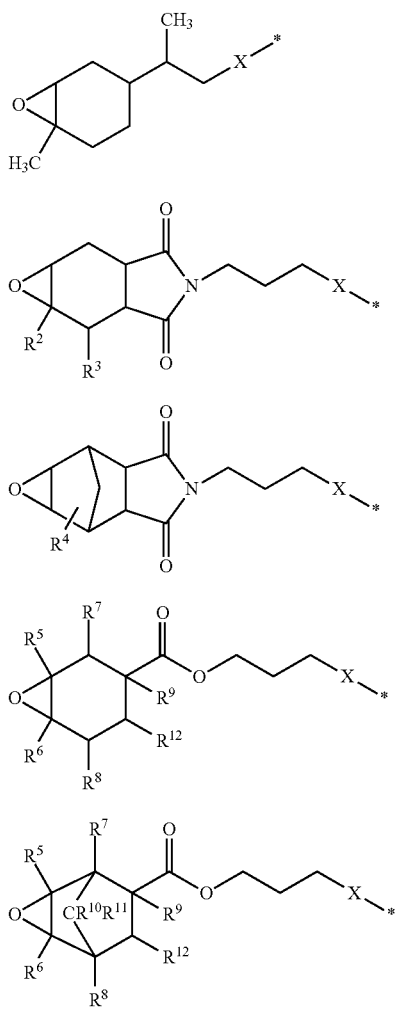

In Formulas (1a) to (5a), R$^2$ and R$^3$ each represent independently a hydrogen atom, an alkyl group having 1 to 6 carbon atoms or a trialkylsilyl group having 1 to 4 carbon atoms. R$^2$ and R$^3$ include, to be specific, a hydrogen atom, methyl, ethyl, propyl, isopropyl, butyl, isobutyl, tertiary butyl, pentyl, hexyl, trimethylsilyl, triethylsilyl and tertiary butyldimethylsilyl, but they shall not be restricted to the above groups. Among them, a hydrogen atom, methyl, trimethylsilyl and tertiary butyldimethylsilyl are preferred, and a hydrogen atom and methyl are more preferred. R$^2$ and R$^3$ may be the same as or different from each other, and they are preferably the same.

R$^4$ represents a hydrogen atom, an alkyl group having 1 to 6 carbon atoms or a trialkylsilyl group having 1 to 4 carbon atoms. R$^4$ includes, to be specific, a hydrogen atom, methyl, ethyl, propyl, isopropyl, butyl, isobutyl, tertiary butyl, pentyl, hexyl, trimethylsilyl, triethylsilyl and tertiary butyldimethylsilyl, but it shall not be restricted to the above groups. Among them, a hydrogen atom, methyl, trimethylsilyl and tertiary butyldimethylsilyl are preferred, and a hydrogen atom and methyl are more preferred.

R$^5$ to R$^{11}$ each represent independently a hydrogen atom, an alkyl group having 1 to 6 carbon atoms or a trialkylsilyl group having 1 to 4 carbon atoms. R$^5$ to R$^{11}$ include, to be specific, a hydrogen atom, methyl, ethyl, propyl, isopropyl, butyl, isobutyl, tertiary butyl, pentyl, hexyl, trimethylsilyl, triethylsilyl and tertiary butyldimethylsilyl, but they shall not be restricted to the above groups. Among them, a hydrogen atom, methyl, trimethylsilyl and tertiary butyldimethylsilyl are preferred, and a hydrogen atom and methyl are more preferred. R$^5$ to R$^{11}$ may be the same as or different from each other, and they are preferably the same.

R$^{12}$ represents a hydrogen atom, an alkyl group having 1 to 6 carbon atoms, a trialkylsilyl group having 1 to 4 carbon atoms or an aryl group. R$^{12}$ includes, to be specific, a hydrogen atom, methyl, ethyl, propyl, isopropyl, butyl, isobutyl, tertiary butyl, pentyl, hexyl, trimethylsilyl, triethylsilyl, tertiary butyldimethylsilyl and phenyl, but it shall not be restricted to the above groups. Among them, a hydrogen atom, methyl, trimethylsilyl, tertiary butyldimethylsilyl and phenyl are preferred, and a hydrogen atom, methyl and phenyl are more preferred.

\* represents a bonding part with Si shown in Formula (I), and —X—\* represents —\* in which X is a single bond or a group represented by Formula (x) shown below:

[Ka 13]

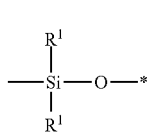

In Formula (x), R$^1$ represents an alkyl group having 1 to 5 carbon atoms, and it is preferably an alkyl group having 1 or 2 carbon atoms. R$^1$ includes, to be specific, methyl, ethyl, propyl, isopropyl, butyl and pentyl, but it shall not be restricted to the above groups. Among them, methyl and ethyl are preferred.

The epoxy compound represented by Formula (I) has n groups of Y. At least one of them, that is, p (p is a natural number equal to n or less) groups of Y are, as described above, groups represented by any of Formulas (1a) to (5a). Among them, Y is preferably a group represented by any of Formulas (1a), (4a) and (5a), more preferably a group represented by Formula (4a).

Among the epoxy compounds of the present invention represented by Formula (I), the epoxy compounds in which R$^1$ is methyl or ethyl are preferred. Also, the epoxy compounds in which R$^2$ to R$^{11}$ each are independently a hydrogen atom or methyl and in which $R^{12}$ is a hydrogen atom, methyl or phenyl are preferred. Further, the epoxy compounds in which at the same time as $R^1$ is methyl or ethyl, $R^2$ to $R^{11}$ each are independently a hydrogen atom or methyl and in which $R^{12}$ is a hydrogen atom, methyl or phenyl are more preferred.

As described above, the epoxy compound of the present invention is, as represented by Formula (I), a so-called alicyclic epoxy compound having an alicyclic epoxy group. Further, the epoxy compound of the present invention is preferably an epoxy compound having a cage-like silsesquioxane structure or a ladder-like silsesquioxane structure.

In a case other than a case where all n groups of Y in the epoxy compound represented by Formula (I) are groups represented by any of Formulas (1a) to (5a) described above, that is, a case where p is a natural number smaller than n, the epoxy compound represented by Formula (I) has (n-p) groups of Y different from the groups represented by Formulas (1a) to (5a). The above (n-p) groups of Y are a hydrogen atom or —$OSiR^1_2H$. In this respect, $R^1$ represents the same alkyl group having 1 to 5 carbon atoms as $R^1$ in Formula (x). In a production process for the epoxy compound represented by Formula (I) described later, (n-p) groups of Y are a residue originating in the polysilicone compound which is a raw material for producing the epoxy compound represented by Formula (I).

<<Epoxy Compound Having a Cage-Like Silsesquioxane Structure>>

The epoxy compound having a cage-like silsesquioxane structure preferably includes, for example, an epoxy compound represented by Formula (II) shown below, that is, the epoxy compound in which n is 8 in Formula (I) described above:

[Ka 14]

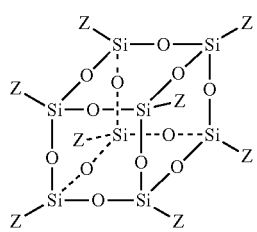
(II)

In Formula (II), q (q is a natural number equal to 8 or less) groups out of 8 groups of Z represent —$OSiR^1_2Y^1$, and $R^1$ represents an alkyl group having 1 to 5 carbon atoms and has the same meaning as that of $R^1$ in Formula (x); and $Y^1$ represents a group represented by any of Formulas (1b) to (5b) shown below:

[Ka 15]

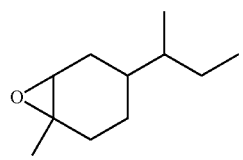
(1b)

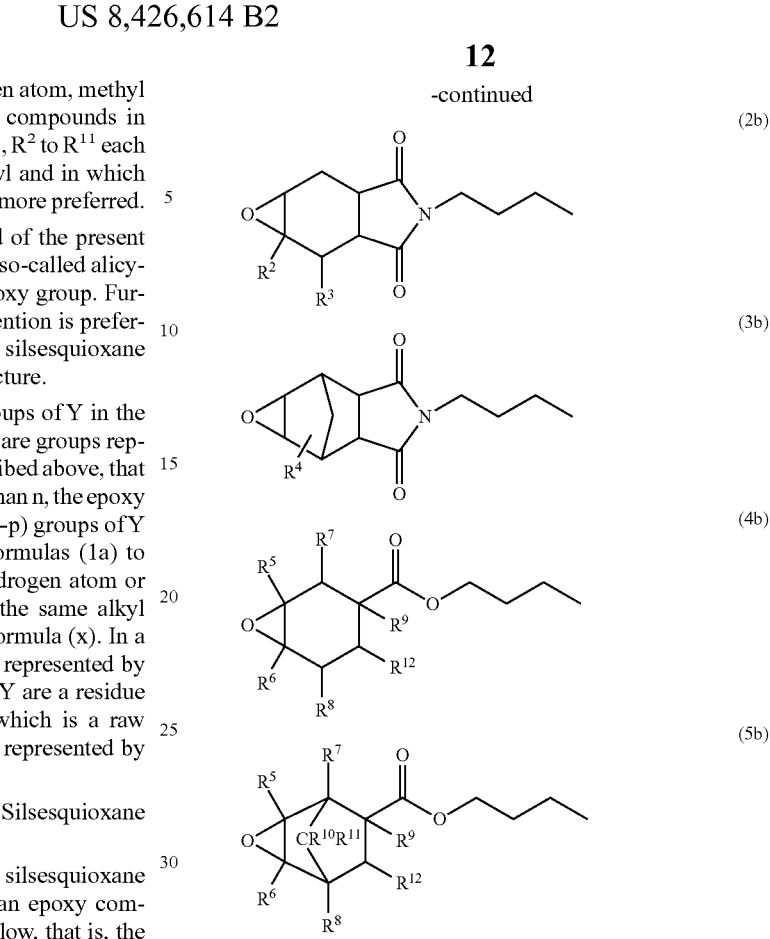

In Formulas (1b) to (5b), $R^2$ and $R^3$ each represent independently a hydrogen atom, an alkyl group having 1 to 6 carbon atoms or a trialkylsilyl group having 1 to 4 carbon atoms and have the same meanings as those of $R^2$ and $R^3$ in Formula (1a) to (5a) described above.

$R^4$ represents a hydrogen atom, an alkyl group having 1 to 6 carbon atoms or a trialkylsilyl group having 1 to 4 carbon atoms and has the same meaning as that of $R^4$ in Formula (1a) to (5a) described above. $R^5$ to $R^{11}$ each represent independently a hydrogen atom, an alkyl group having 1 to 6 carbon atoms or a trialkylsilyl group having 1 to 4 carbon atoms and have the same meanings as those of $R^5$ to $R^{11}$ in Formula (1a) to (5a) described above.

$R^{12}$ represents a hydrogen atom, an alkyl group having 1 to 6 carbon atoms, a trialkylsilyl group having 1 to 4 carbon atoms or an aryl group and has the same meaning as that of $R^{12}$ in Formula (1a) to (5a) described above.

$Y^1$ is, as described above, a group represented by any of Formulas (1b) to (5b) shown below, and among them, it is preferably a group represented by any of Formulas (1b), (4b) and (5b), more preferably a group represented by Formula (4b).

Among the epoxy compounds of the present invention represented by Formula (II), the epoxy compounds in which $R^1$ is methyl or ethyl are preferred. Also, the epoxy compounds in which $R^2$ to $R^{11}$ each are independently a hydrogen atom or methyl and in which $R^{12}$ is a hydrogen atom, methyl or phenyl are preferred. Further, the epoxy compounds in which at the same time as $R^1$ is methyl or ethyl, $R^2$ to $R^{11}$ each are independently a hydrogen atom or methyl and in which $R^{12}$ is a hydrogen atom, methyl or phenyl are more preferred.

In a case other than a case where all 8 groups of Z in the epoxy compound represented by Formula (II) are groups represented by any of Formulas (1b) to (5b) described above, that is, a case where q is a natural number smaller than 8, the epoxy compound represented by Formula (II) has (8−q) groups of Z different from the groups represented by Formulas (1b) to (5b). The above (8−q) groups of Z are —OSiR$^1_2$H. In this respect, R$^1$ represents the same alkyl group having 1 to 5 carbon atoms as R$^1$ in Formula (x). In a production process for the epoxy compound represented by Formula (II) described later, (8−q) groups of Z are a residue originating in the polysilicone compound which is a raw material for producing the epoxy compound represented by Formula (II).

<<Epoxy Compound Having a Ladder-Like Silsesquioxane Structure>>

The epoxy compound having a ladder-like silsesquioxane structure preferably includes, for example, an epoxy compound represented by Formula (II') shown below, but it shall not be restricted to these compounds:

[Ka 16]

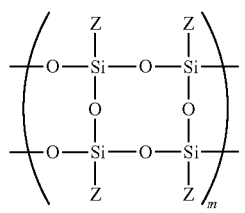

(II')

In Formula (II'), m is an integer of 2 to 125, preferably 2 to 50 and more preferably 2 to 30. Z has the same meaning as in Formula (II) described above. That is, the epoxy compound represented by Formula (II') corresponds to the epoxy compound in which n is 8 to 500 in Formula (I) described above. The compound represented by Formula (II') has 4m groups of Z, and in a case other than a case where all 4m groups of Z are the groups represented by any of Formulas (1b) to (5b) described above, the epoxy compound represented by Formula (II') has Z different from the groups represented by any of Formulas (1b) to (5b) described above. In the above case, Z different from the groups represented by any of Formulas (1b) to (5b) described above is —OSiR$^1_2$H. In this respect, R$^1$ represents the same alkyl group having 1 to 5 carbon atoms as R$^1$ in Formula (x). In a production process for the epoxy compound represented by Formula (II') described later, Z different from the groups represented by any of Formulas (1b) to (5b) is a residue originating in the polysilicone compound which is a raw material for producing the epoxy compound represented by Formula (II').

As described above, the epoxy compound of the present invention is a so-called alicyclic epoxy compound having an alicyclic epoxy group, and therefore it has a high storage stability as compared with that of an epoxy compound of a glycidyl type and is easily used in an industrial scale. Further, the above alicyclic epoxy group has a higher cationic polymerizability than a usual glycidyl group and therefore can be cured at lower temperature for shorter time.

The epoxy compound of the present invention is liquid at room temperature, that is, 10 to 30° C. Accordingly, it can suitably be used for applications such as UV nanoimprint which is required to be liquid. The term "to be liquid" means that the viscosity (mPa·s) can be measured, after removing a solvent and the like, by means of a viscosity measuring equipment (VISCOMETER DV-II+Pro, manufactured by BROOKFIELD ENGINEERING LABORATORIES, INC.), and the above viscosity is usually 1000 to 30000 mPa·s, preferably 5000 to 20000 mPa·s.

<Process for Producing the Epoxy Compound>

The process for producing the epoxy compound of the present invention is characterized by comprising the step of reacting the polysilicone compound represented by Formula (III) or the polysilicone compound represented by Formula (IV) with the epoxy compound represented by any of Formulas (6) to (10) shown below at 10 to 200° C. That is, the above reaction is hydrosilylation reaction and can be allowed to proceed sufficiently even at about room temperature.

[Ka 17]

(III)

In Formula (III), Y$^1$ represents a hydrogen atom or —OSiR$^1_2$H; R$^1$ represents an alkyl group having 1 to 5 carbon atoms.

In Formula (III), n represents an integer of 2 to 500, preferably an even number of 6 to 18 and more preferably 8.

[Ka 18]

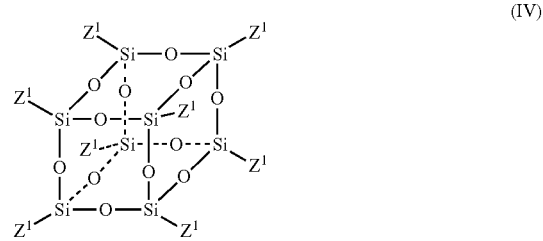

(IV)

In Formula (IV), Z$^1$ represents —OSiR$^1_2$H, and R$^1$ represents an alkyl group having 1 to 5 carbon atoms.

[Ka 19]

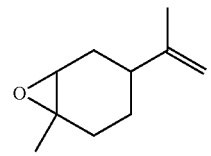

(6)

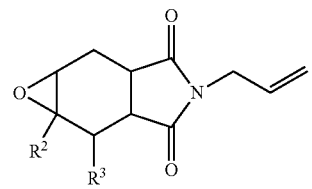

(7)

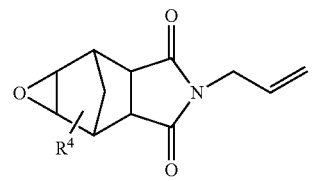

(8)

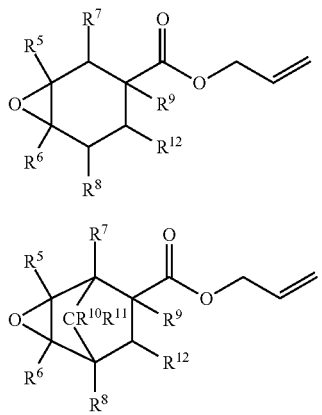

(9)

(10)

In Formulas (6) to (10), $R^2$ and $R^3$ each represent independently a hydrogen atom, an alkyl group having 1 to 6 carbon atoms or a trialkylsilyl group having 1 to 4 carbon atoms and have the same meanings as those of $R^2$ and $R^3$ in Formula (1a) to (5a) described above.

$R^4$ represents a hydrogen atom, an alkyl group having 1 to 6 carbon atoms or a trialkylsilyl group having 1 to 4 carbon atoms and has the same meaning as that of $R^4$ in Formula (1a) to (5a) described above.

$R^5$ to $R^{11}$ each represent independently a hydrogen atom, an alkyl group having 1 to 6 carbon atoms or a trialkylsilyl group having 1 to 4 carbon atoms and have the same meanings as those of $R^5$ to $R^{11}$ in Formula (1a) to (5a) described above.

$R^{12}$ represents a hydrogen atom, an alkyl group having 1 to 6 carbon atoms, a trialkylsilyl group having 1 to 4 carbon atoms or an aryl group and has the same meaning as that of $R^{12}$ in Formula (1a) to (5a) described above.

<<Polysilicone Compound>>

The polysilicone compound represented by Formula (III) described above is preferably a polysilicone compound having a cage-like silsesquioxane structure or a ladder-like silsesquioxane structure.

The polysilicone compound having a ladder-like silsesquioxane structure includes, for example, a polysilicone compound represented by Formula (III') shown below, but it shall not be restricted thereto:

[Ka 20]

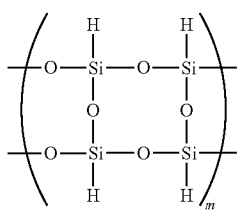

(III')

In Formula (III'), m is an integer of 2 to 125, preferably 2 to 50 and more preferably 2 to 30. That is, it corresponds to the polysilicone compound in which n is 8 to 500 in Formula (III) described above.

A polysilicone compound having a cage-like silsesquioxane structure other than the polysilicone compound having a cage-like silsesquioxane structure represented by Formula (III) described above includes preferably, for example, a polysilicone compound represented by Formula (IV) shown below:

[Ka 21]

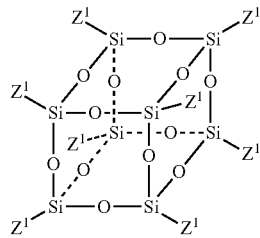

(IV)

In Formula (IV), $Z^1$ represents $-OSiR^1_2H$, and $R^1$ is an alkyl group having 1 to 5 carbon atoms, and it is preferably an alkyl group having 1 or 2 carbon atoms. $R^1$ includes, to be specific, methyl, ethyl, propyl, isopropyl, butyl and pentyl, but it shall not be restricted to the above groups. Among them, methyl and ethyl are preferred.

<<Epoxy Compound>>

The epoxy compound described above is a compound having a double bond represented by any of Formulas (6) to (10), and among them, it is preferably a compound represented by any of Formulas (6), (9) and (10), more preferably a compound represented by Formula (9).

Also, the epoxy compound in which $R^2$ to $R^{11}$ each are independently a hydrogen atom or methyl and in which $R^{12}$ is a hydrogen atom, methyl or phenyl is preferred.

A combination of the polysilicone compound and the polysilicone compound each described above is preferably a combination of the polysilicone compound represented by Formula (IV) in which $R^1$ is methyl or ethyl and the polysilicone compound in which $R^2$ to $R^{11}$ each are independently a hydrogen atom or methyl and in which $R^{12}$ is a hydrogen atom, methyl or phenyl.

A blending ratio of the polysilicone compound represented by Formula (III) or (IV) to the epoxy compound having a double bond represented by any of Formulas (6) to (10) described above is optional and shall not specifically be restricted, and a SiH group in the polysilicone compound described above is blended in an equivalent of usually 0.3 to 1.5 time, preferably 0.3 to 1.1 time based on 1 equivalent of an ethylenical double bond in the epoxy compound described above. If the blending amount thereof falls outside the range described above, one of the above compounds remains as it is unreacted, and therefore it is economically disadvantageous in a certain case.

An addition reaction catalyst comprising transition metals such as platinum, rhodium, palladium, nickel, iridium, ruthenium and the like or compounds thereof can be selected as a catalyst used for reaction of the polysilicone compound with the epoxy compound, that is, hydrosilylation reaction. To be specific, it includes chloroplatinic acid, various complexes of platinum, complexes of platinum and vinylsiloxane excluding chlorine, Karsted catalysts, various solutions of platinum compounds (solutions prepared by dissolving or dispersing the compounds in alcohols, ketones, ethers, esters, aromatic hydrocarbons and the like), Speier catalysts, catalysts prepared by carrying components on various solid supports (silica gel, activated carbon and the like), Rh catalysts such as Wilkinson complexes and the like and various complex catalysts of palladium, and the kind or the form thereof shall not be restricted.

For example, when a platinum catalyst is used, a use amount thereof shall not specifically be restricted, and an amount of a platinum atom is usually $1 \times 10^{-2}$ to $10^{-8}$ time mole, preferably $1 \times 10^{-2}$ to $10^{-6}$ time mole based on a mole number of hydroalkoxysilane. If an amount of a platinum atom is less than the lower limit value described above, the reaction rate is extremely reduced in a certain case. If it exceeds the upper limit value described above, the reaction rate is elevated, but a ring opening reaction of the epoxy group is likely to be brought about, and it is economically disadvantageous in a certain case.

A solvent does not necessarily have to be used in the production process of the present invention, but the solvent may be used, if necessary, as a reaction solvent or a medium for the catalyst solution. The solvent can be used according to necessity such as dissolving or diluting the polysilicone compound or the epoxy compound described above, controlling a temperature of the reaction system, securing a volume necessary for stirring and facilitating addition of the catalyst. The above solvent includes, to be specific, saturated hydrocarbons such as pentane, hexane, isooctane, decane, cyclohexane and the like, aromatic hydrocarbons such as toluene, xylene, mesitylene, ethylbenzene, decalin, tetralin and the like, ethers such as diethyl ether, THF and the like, esters and various silicones such as polydimethylsiloxane and the like. Among them, the solvent can optionally be selected, and a use amount thereof may optionally be determined. The above solvents may be used alone or in a mixture of two or more kinds thereof.

In order to carry out reaction of the polysilicone compound with the epoxy compound, that is, hydrosilylation reaction, a reaction vessel filled sufficiently with an inert gas such as a dried nitrogen gas and the like is first charged usually with the epoxy compound represented by any of Formulas (6) to (10) and the catalyst. In this case, solvents may be added thereto if necessary. Then, after the reaction vessel is heated up to a prescribed temperature while stirring, the polysilicone compound represented by Formula (III) or (IV) is dropwise added to the mixture described above to subject them to addition reaction, and after finishing dropwise addition, the solution is ripened until the reaction is completed.

Allowed to be employed as well is a method in which the reaction vessel described above is first charged with the polysilicone compound represented by Formula (III) or (IV) and in which the epoxy compound represented by any of Formulas (6) to (10) is then added thereto. Also, allowed to be employed as well is a method in which a mixed solution of the polysilicone compound represented by Formula (III) or (IV) and the epoxy compound represented by any of Formulas (6) to (10) is added to the catalyst and/or the solvent, and a method in which the reaction vessel is charged with all of the raw materials in a lump sum and then heated may be employed as well. Further, the production process of the present invention can be applied in a reaction manner of any of a batch system, a continuous system and a semi-continuous system.

The reaction temperature falls in a range of 10 to 200° C., particularly preferably 10 to 150° C. If the reaction temperature is lower than the lower limit value described above, the reaction rate is reduced, and the reaction is not completed within a practical process time in a certain case. Further, if the reaction temperature exceeds the upper limit value described above, the reaction rate is elevated, but a ring opening polymerization of an epoxy group of the epoxy compound represented by any of Formulas (6) to (10) or the epoxy compound which is the targeted product is brought about a certain case.

Usually, an atmospheric pressure condition is sufficient for the pressure condition, and this condition is preferred in terms of the operability and the economical efficiency. However, the reaction may be carried out, if necessary, under applied pressure.

An atmosphere in the reaction vessel is preferably an atmosphere of an inert gas such as a nitrogen gas and the like. Mixing-in of moisture (or air containing moisture) not only exerts an adverse effect on the reaction but also hydrolyzes the polysilicone compound represented by Formula (III), and a yield of the epoxy compound which is the targeted product is likely to be reduced. A publicly known technique in which dried air or an inert gas containing oxygen is introduced into the reaction atmosphere for the purpose of enhancing the catalyst activity in the addition reaction may be applied.

The reaction time can be varied according to the reaction temperature, the pressure conditions, the catalyst concentration and the concentrations of the raw materials in the reaction system and is usually 0.1 to 100 hours, and the reaction time can optionally be selected in the range described above.

As described above, the epoxy compound of the present invention represented by Formula (I) or (II) is obtained by subjecting the polysilicone compound represented by Formula (III) or the polysilicone compound represented by Formula (IV) to hydrosilylation reaction with the epoxy compound represented by any of Formulas (6) to (10) at 10 to 200° C.

The epoxy compound represented by Formula (I) which is obtained by the above reaction has n groups of Y but includes as well a case other than a case where all n groups of Y are groups originating in the compounds represented by any of Formulas (6) to (10). That is, the epoxy compound obtained by the above reaction is at least one of the compounds in which p (p is a natural number equal to n or less, that is, a natural number of 1 to n) groups out of n groups of Y contained in the above compound are the groups represented by any of Formulas (1a) to (5a), and it is obtained in the form of a mixture of the epoxy compounds having different p in many cases. In a case other than a case where all n groups of Y in the epoxy compound obtained by the above reaction are groups originating in the compounds represented by any of Formulas (6) to (10), the above epoxy compound has (n–p) groups of Y different from the groups represented by Formulas (1a) to (5a). In the above case, (n–p) groups of Y are hydrogen atoms of the polysilicone compound represented by Formula (III) which is the raw material in the above reaction, and they are unreacted hydrogen atoms.

Similarly, the epoxy compound represented by Formula (II) which is obtained by the above reaction has 8 groups of Z but includes a case other than a case where all 8 groups of Z are the compounds represented by any of Formulas (6) to (10). That is, the epoxy compound obtained by the above reaction is at least one of the compounds in which q (q is a natural number equal to 8 or less, that is, a natural number of 1 to 8) groups out of 8 groups of Z contained in the above compound are the groups represented by any of Formulas (1a) to (5a), and a mixture of the epoxy compounds having different q is obtained in many cases. In a case other than a case where all q groups of Z in the epoxy compound obtained by the above reaction are groups originating in the compounds represented by any of Formulas (6) to (10), the above epoxy compound has (8–q) groups of Z different from the groups represented by Formulas (1a) to (5a). In the above case, (8–q) groups of Z are $Z^1$ of the polysilicone compound represented by Formula (IV) which is the raw material in the above reaction, that is, —OSi$R^1{}_2$H, and they are unreacted $Z^1$.

A conventional method can be used for refining the products. It includes, for example, an adsorption separation method and includes, to be specific, a method in which an adsorbent such as activated carbon, acid clay, activated clay and the like is used. In addition to the above method, it includes an adsorption removing method for impurities and colored substances or column chromatography and thin layer chromatography. The adsorption removing method includes, to be specific, an adsorption removing method in which silica gel, hydrous silica gel, alumina, activated carbon, titania and zirconia are used. The column chromatography includes column chromatography in which the above silica gel, hydrous silica gel and alumina are used as a filler. Further, the products can be refined as well by distillation such as distillation under reduced pressure, molecular distillation and the like. A small amount of amines, sulfur-containing compounds and the like may be added to the reaction liquid before distillation as a publicly known means for inhibiting ring-opening polymerization of the epoxy groups of the epoxy compound of the present invention under distillation and the epoxy compound represented by any of Formulas (6) to (10) which is the raw material. Further, the products are not necessarily required to be refined depending on the use purposes of the epoxy compound of the present invention, and they may be used in the form of the reaction mixture.

A reaction vessel in the present invention shall not specifically be restricted, but it is preferably equipped with devices such as a stirring device, a thermometer, a reflux condenser, a dropping device and the like.

EXAMPLES

The present invention shall be explained below in detail with reference to examples, but the present invention shall not be restricted to these examples.

In the examples and the comparative examples, the following items were measured and evaluated on the following conditions and standards.

<<DSC (Differential Scanning Calorimetry) Measuring Conditions>>
Equipment: differential scanning calorimeter EXSTAR6000 DSC (manufactured by SII NanoTechnology Inc.)
UV irradiation equipment: UV-1 (manufactured by SII Nano Technology Inc.)
UV illuminance: 6.0 mw/cm$^2$ or 7.8 mw/cm$^2$
UV irradiation time: 20 minutes <<Measuring Method for Reactive Ion Etching Rate>>
A small piece of glass was adhered on a cured thin film and subjected to etching treatment according to the following conditions. A small piece of glass was detached, and a step between a thin film part protected by a small piece of glass and an etched thin film part was measured. The etching rate was determined from a treating time of reactive ion etching and the step according to the following equation:

etching rate (nm/second)=step (nm)÷treating time (second)

Conditions of reactive ion etching:
Fluorine base gas:
  Etching gas: carbon tetrafluoride
  Pressure: 0.5 Pa
  Gas flow amount: 40 sccm
  Plasma voltage: 200 W
  Bias voltage: 20 W
  Treating time: 30 seconds
Oxygen:
  Etching gas: oxygen
  Pressure: 0.5 Pa
  Gas flow amount: 40 sccm
  Plasma voltage: 200 W
  Bias voltage: 20 W
  Treating time: 600 seconds <<Viscosity Measurement>>
Measuring equipment: VISCOMETER DV-II+Pro (manufactured by BROOKFIELD ENGINEERING LABORATORIES, INC.)
Measuring temperature: 24.9° C.

Preparation Example 1

A three neck flask of 500 mL equipped with a reflux condenser, a thermometer, a stirring device, a dropping funnel and an oil bath was charged with 100.0 g of allyl 3-cyclohexene-1-carboxylate, 2.34 g of methyl hydrogensulfate trioctylammonium, 3.96 g of sodium tungstate dihydrate and 0.45 g of aminomethylphosphonic acid. The flask was heated on the oil bath maintained at 90° C., and 80 ml of 30% aqueous hydrogen peroxide was dropwise added thereto through the dropping funnel in 180 minutes to ripen the solution as it was for 4 hours. The flask was cooled on an ice bath, and surplus hydrogen peroxide was removed by 300 ml of a saturated sodium thiosulfate aqueous solution. Then, the solution was extracted twice with 200 ml of ethyl acetate. The ethyl acetate solution thus obtained was dried on anhydrous sodium sulfate for a night, and ethyl acetate which was the solvent was removed by means of a rotary evaporator. Then, the residue was refined by a silica gel chromatography filled with 25% hydrous silica gel to obtain 79.6 g of allyl 3,4-epoxycyclohexane-1-carboxylate.

Example 1

A three neck flask of 50 ml equipped with a reflux condenser, a thermometer, a stirring device and a serum cap was charged with 1.0 g (0.98 mmol) of PSS-octakis(dimethylsilyloxy) substituted (1,3,5,7,9,11,13,15-octakis(dimethylsilyloxy)pentacyclo[9.5.1.1$^{3,9}$.1$^{5,15}$.1$^{7,13}$]-octasiloxane, manufactured by Sigma-Aldrich Corporation) as the polysilicone compound in which $R^1$ of eight $Z^1$ in Formula (IV) is methyl, 1.432 g (7.84 mmol) of allyl 3,4-epoxycyclohexane-1-carboxylate obtained in Preparation Example 1 and 5.0 ml of toluene, and the mixture was stirred at room temperature (25° C.) under argon flow (a —SiH group contained in PSS-octakis(dimethylsilyloxy) substituted corresponds to 1 equivalent based on 1 equivalent of an ethylenical double bond contained in allyl 3,4-epoxycyclohexane-1-carboxylate). A 2% divinyltetramethyldisiloxane platinum complex xylene solution 0.00093 g (0.02 mol %) was slowly dropwise added to the above mixed solution by means of a syringe, and the mixture was stirred at room temperature (25° C.). Stirring was continued for 2 hours while maintaining the above temperature, and then the toluene solvent was removed under reduced pressure to obtain an epoxy compound represented by Formula (V) shown below (hereinafter referred to as an epoxy compound (V), theoretical molecular weight=2474.4 assuming that all of 8 groups of A were reacted) as a nonvolatile component:

[Ka 22]

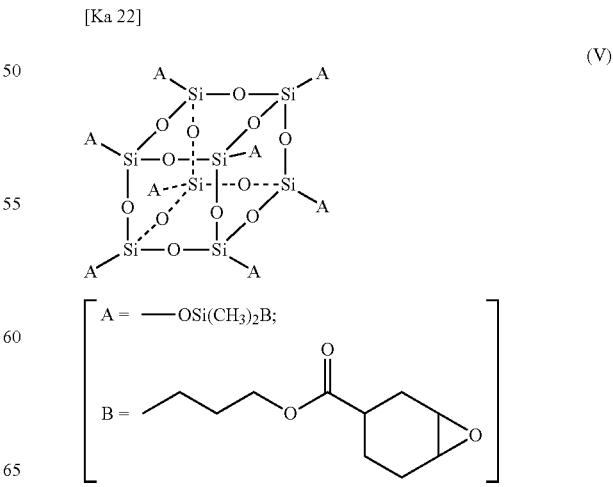

Comparative Example 1

A bisphenol A type liquid epoxy resin (Epikote 828US, hereinafter referred to as an epoxy resin X, manufactured by Japan Epoxy Resins Co., Ltd.) was used in place of the epoxy compound.

<<Measurement and Evaluation of Reactive Ion Etching Rate; <Example 1 and Comparative Example 1>>>

The epoxy compound (V) obtained in Example 1 was dissolved in propylene glycol monomethyl ether acetate so that a nonvolatile component concentration was 10% by mass, and triphenylsulfonium hexafluoroantimonate which was an optical cationic polymerization initiator was added to the solution in an amount of 1 part by mass based on 100 parts by mass of the nonvolatile component and dissolved therein. Then, the solution was filtrated through a filter of 0.2 µm, and 0.5 ml thereof was dropped on a glass substrate set in a spin coater. The glass substrate was rotated at 500 rpm for 5 seconds, then at 3000 rpm for 2 seconds and further at 5000 rpm for 20 seconds, whereby a thin film of the epoxy compound (V) was formed on the glass substrate. The glass substrate on which a thin film of the epoxy compound (V) was formed was irradiated with a UV ray under nitrogen flow. A cured thin film of the epoxy compound (V) thus obtained was used to measure a reactive ion etching rate with a $CF_4$ gas and oxygen. The results thereof are shown in Table 1.

Also, dissolved were 100 parts by mass of the epoxy resin X obtained in Comparative Example 1, 1 part by mass of triphenylsulfonium hexafluoroantimonate which was an optical cationic polymerization initiator and 900 parts by mass of propylene glycol monomethyl ether acetate, and the solution was filtrated through a filter of 0.2 µm, and 0.5 ml thereof was dropwise added on a glass substrate set in a spin coater. The glass substrate was rotated at 500 rpm for 5 seconds, then at 3000 rpm for 2 seconds and further at 5000 rpm for 20 seconds, whereby a thin film was formed on the glass substrate. The glass substrate was irradiated with a UV ray under nitrogen flow. A cured thin film of the epoxy resin X thus obtained was used to measure a reactive ion etching rate with a $CF_4$ gas and oxygen. The results thereof are shown in Table 1.

TABLE 1

|  | Example 1 | Comparative Example 1 |
|---|---|---|
| $O_2$ etching rate (nm/sec) | 0.03 | 3.11 |
| $CF_4$ etching rate (nm/sec) | 1.45 | 0.88 |

The thin film prepared by using the epoxy compound (V) obtained in Example 1 has a low rate of oxygen etching and a high rate of fluorine base etching as compared with those of the thin film prepared by using the epoxy resin X obtained in Comparative Example 1. As shown above, it can be found that the epoxy compound (V) has a high durability against oxygen etching, so that it has a very high selectivity and can suitably be used as a resist.

Comparative Example 2

A three neck flask of 100 ml equipped with a reflux condenser, a thermometer, a stirring device and a serum cap was charged with 1.0 g (0.98 mmol) of PSS-octakis(dimethylsilyloxy) substituted, 0.897 g (7.84 mmol) of allyl glycidyl ether and 5.0 ml of toluene, and the mixture was stirred at room temperature (25° C.) under argon flow. A 2% divinyltetramethyldisiloxane platinum complex xylene solution 0.00093 g (0.02 mol %) was slowly dropwise added to the above mixed solution by means of a syringe, and the mixture was stirred at room temperature (25° C.). Stirring was continued for 2 hours while maintaining the above temperature, and then the toluene solvent was removed under reduced pressure to obtain an epoxy compound represented by Formula (VI) shown below (hereinafter referred to as an epoxy compound (VI)) as a nonvolatile component:

[Ka 23]

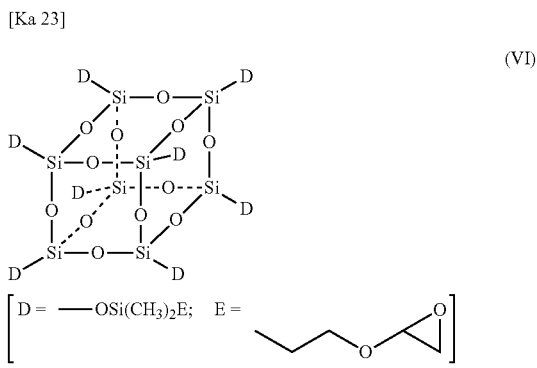

(VI)

<<DSC Measurement and Evaluation; <Example 1 and Comparative Example 2>>>

Triphenylsulfonium hexafluoroantimonate 1 part by mass which was an optical cationic polymerization initiator was added to the epoxy compound (V) 100 parts by mass obtained in Example 1 to measure DSC. The UV illuminance was set to 6.0 mw/cm². The charts of DSC and DDSC thus obtained are shown in FIG. 1.

Further, DSC of the epoxy compound (VI) obtained in Comparative Example 2 was measured in the same manner as in the epoxy compound (V) described above. The charts of DSC and DDSC thus obtained are shown in FIG. 2.

Figure 2:
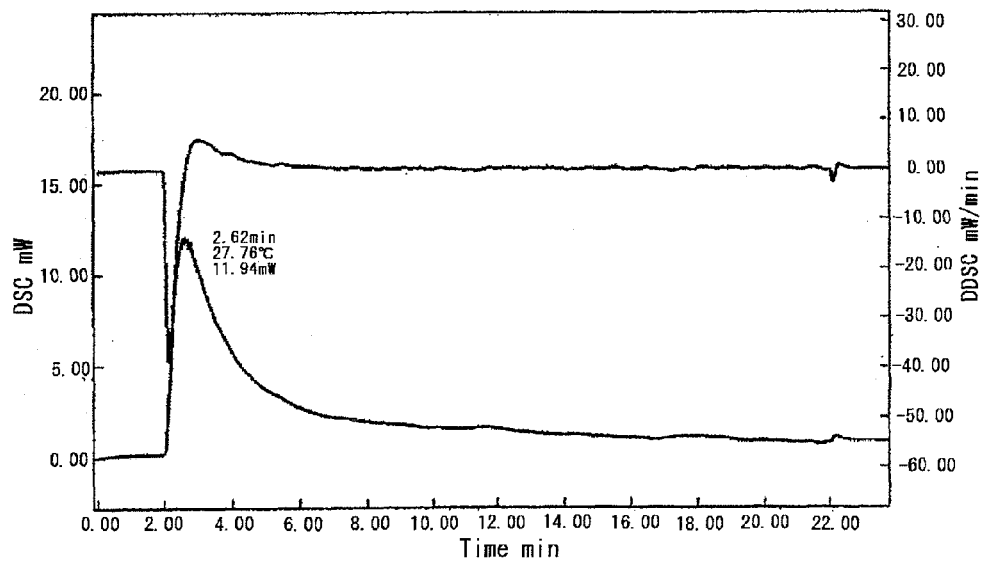
FIG. 2 is chart diagrams of DSC and DDSC of the epoxy compound (VI) obtained in Comparative Example 2.
Figure 3:
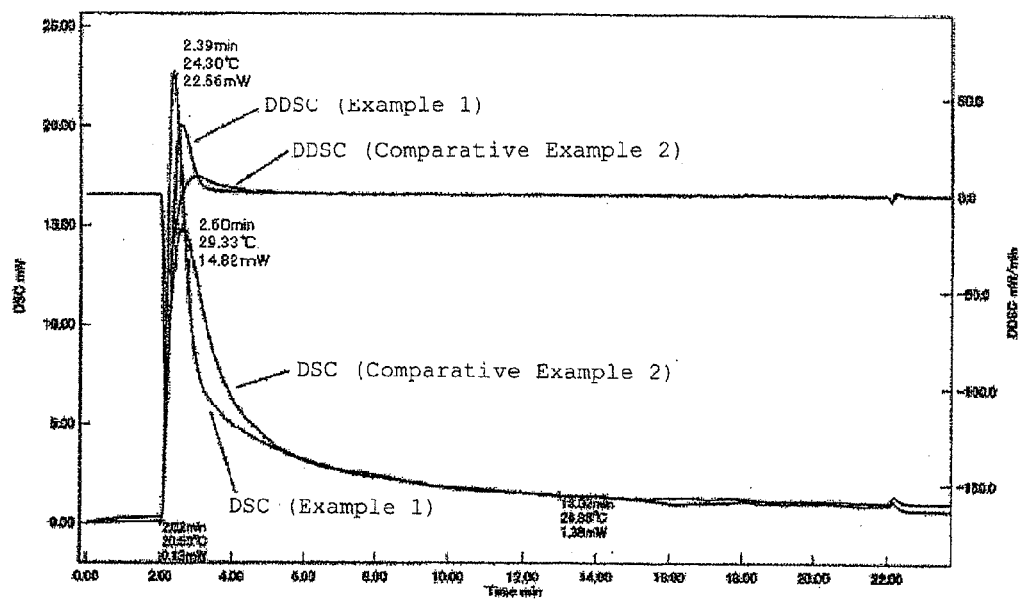
FIG. 3 is a comparison chart diagram obtained by superposing the respective charts of FIG. 1 and FIG. 2.

Further, a comparison chart obtained by superposing the respective charts shown in FIG. 1 and FIG. 2 is shown in FIG. 3. As can be seen from the above chart, in a case of DSC, an end point of an exothermic peak is present at a shorter time in a DSC curve of the epoxy compound (V) obtained in Example 1 than in a DSC curve of the epoxy compound (VI) obtained in Comparative Example 2, and it can be found from the above matter that the polymerization reaction is finished earlier in the epoxy compound (V). Also, in a case of DDSC, an end point of an exothermic change is present at a shorter time in a DDSC curve of the epoxy compound (V) obtained in Example 1 than in a DDSC curve of the epoxy compound (VI) obtained in Comparative Example 2, and it can be found as well from the above matter that the polymerization reaction is finished earlier in the epoxy compound (V).

That is, it is shown that the epoxy compound (V) of the present invention having an alicyclic epoxy group is cured by UV more quickly than the epoxy compound (VI) having an epoxy group of a glycidyl type.

Example 2

A three neck flask of 100 ml equipped with a reflux condenser, a thermometer, a stirring device and a serum cap was charged with 1.0 g (0.98 mmol) of PSS-octakis(dimethylsilyloxy) substituted, 1.1966 g (7.84 mmol) of limonene oxide and 5.0 ml of toluene, and the mixture was stirred at room temperature (25° C.) under argon flow (a —SiH group contained in PSS-octakis(dimethylsilyloxy) substituted corresponds to 1 equivalent based on 1 equivalent of an ethylenical double bond contained in limonene oxide). A 2% divinyltetramethyldisiloxane platinum complex xylene solution 0.00093 g (0.02 mol %) was slowly dropwise added to the above mixed solution by means of a syringe, and the mixture was stirred at room temperature (25° C.). Stirring was continued for 2 hours while maintaining the above temperature, and then the toluene solvent was removed under reduced pressure to obtain an epoxy compound represented by Formula (VII) shown below (hereinafter referred to as an epoxy compound (VII), theoretical molecular weight=2234.4 assuming that all of 8 groups of J were reacted) as a nonvolatile component:

[Ka 24]

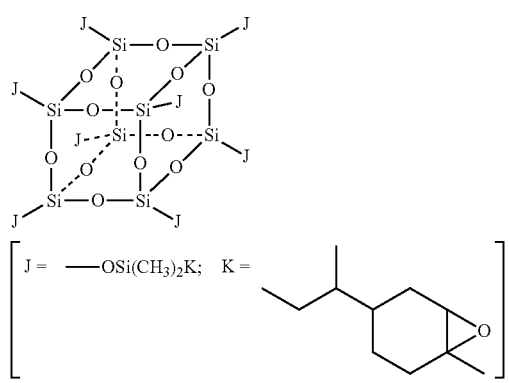

(VII)

<<Measurement and Evaluation of Reactive Ion Etching Rate; <Example 2>>>

The epoxy compound (VII) obtained in Example 2 was dissolved in propylene glycol monomethyl ether acetate so that a nonvolatile component concentration was 10% by mass, and triphenylsulfonium hexafluoroantimonate which was an optical cationic polymerization initiator was added to the solution in an amount of 1 part by mass based on 100 parts by mass of the nonvolatile component and dissolved therein. Then, the solution was filtrated through a filter of 0.2 μm, and 0.5 ml thereof was dropped on a glass substrate set in a spin coater. The glass substrate was rotated at 500 rpm for 5 seconds, then at 3000 rpm for 2 seconds and further at 5000 rpm for 20 seconds, whereby a thin film of the epoxy compound (VII) was formed on the glass substrate. The glass substrate on which a thin film of the epoxy compound (VII) was formed was irradiated with a UV ray under nitrogen flow. A cured thin film of the epoxy compound (VII) thus obtained was used to measure a reactive ion etching rate with a $CF_4$ gas and oxygen. The results thereof are shown in Table 2.

TABLE 2

| | Example 2 |
|---|---|
| $O_2$ etching rate (nm/sec) | 0.03 |
| $CF_4$ etching rate (nm/sec) | 0.78 |

<<DSC Measurement and Evaluation>>

Figure 4:
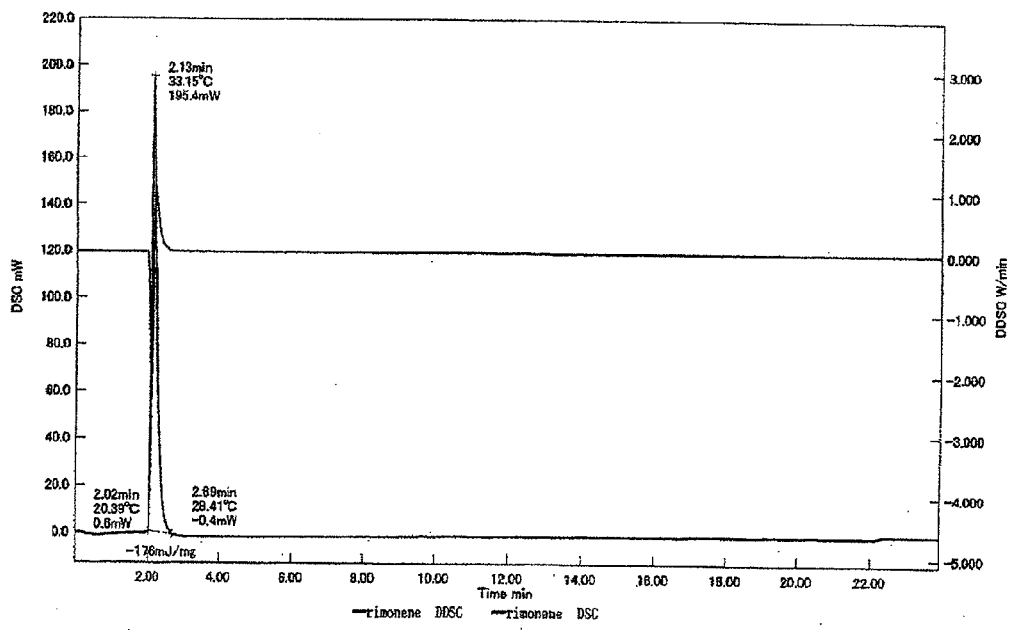
FIG. 4 is a chart diagram of DSC of the epoxy compound (VII) obtained in Example 2.

Triphenylsulfonium hexafluoroantimonate 1 part by mass which was an optical cationic polymerization initiator was added to the epoxy compound (VII) 100 parts by mass obtained in Example 2 to measure DSC. The UV illuminance was set to 7.8 mw/cm². The DSC chart obtained is shown in FIG. 4.

As shown above, it can be found that the thin film prepared by using the epoxy compound (VII) obtained in Example 2 has an excellent etching performance to oxygen etching and is shorter in a curing time.

Comparative Example 3

A three neck flask of 100 ml equipped with a reflux condenser, a thermometer, a stirring device and a serum cap was charged with 1.0 g (0.98 mmol) of PSS-octakis(dimethylsilyloxy) substituted, 0.9759 g (7.84 mmol) of 4-vinylcyclohexene oxide and 5.0 ml of toluene, and the mixture was stirred at room temperature (25° C.) under argon flow. A 2% divinyltetramethyldisiloxane platinum complex xylene solution 0.00093 g (0.02 mol %) was slowly dropwise added to the above mixed solution by means of a syringe, and the mixture was stirred at room temperature (25° C.). Stirring was continued at room temperature for 2 hours, and then the toluene solvent was removed under reduced pressure to obtain an epoxy compound represented by Formula (VIII) shown below (hereinafter referred to as an epoxy compound (VIII)):

[Ka 25]

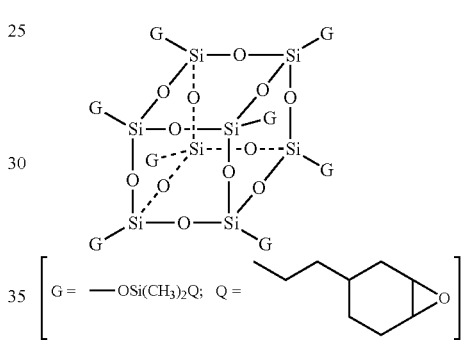

(VIII)

<<Viscosity Measurement and Evaluation; <Examples 1 to 2 and Comparative Example 3>>>

The epoxy compound (V) obtained in Example 1, the epoxy compound (VII) obtained in Example 2 and the epoxy compound (VIII) obtained in Comparative Example 3 were used, and the solvent was completely removed respectively by means of an evaporator and a vacuum pump to measure the viscosities. The results thereof are shown in Table 3.

TABLE 3

| | Example 1 | Example 2 | Comparative Example 3 |
|---|---|---|---|
| State | Liquid | Liquid | Solid |
| Viscosity cP) | 7552 | 16760 | — |

As described above, it is shown that the epoxy compounds prepared in Examples 1 and 2 are liquid at room temperature, and it can be found that they are suited to uses such as resists for UV nanoimprint.

Example 3

A three neck flask of 100 ml equipped with a reflux condenser, a thermometer, a stirring device and a serum cap was charged with 1.429 g (7.84 mmol) of allyl 3,4-epoxycyclohexane-1-carboxylate and 0.00093 g (0.02 mol %) of a 2% divinyltetramethyldisiloxane platinum complex xylene solution, and the mixture was stirred at 60° C. under argon flow. Then, 1.0 g (0.98 mmol) of PSS-octakis(dimethylsilyloxy)

substituted dissolved in 5.0 ml of toluene was slowly added thereto by means of a dropping funnel (a —SiH group contained in PSS-octakis(dimethylsilyloxy) substituted corresponds to 1 equivalent based on 1 equivalent of an ethylenical double bond contained in allyl 3,4-epoxycyclohexene-1-carboxylate). Stirring was continued for 12 hours while maintaining the above temperature, and after confirming by gas chromatography that a whole amount of PSS-octakis(dimethylsilyloxy) substituted was consumed, the reaction was finished. The toluene solvent was removed under reduced pressure, and then unreacted allyl 3,4-epoxycyclohexene-1-carboxylate was removed by means of a thin film distillation equipment to obtain a nonvolatile component.

Figure 5:
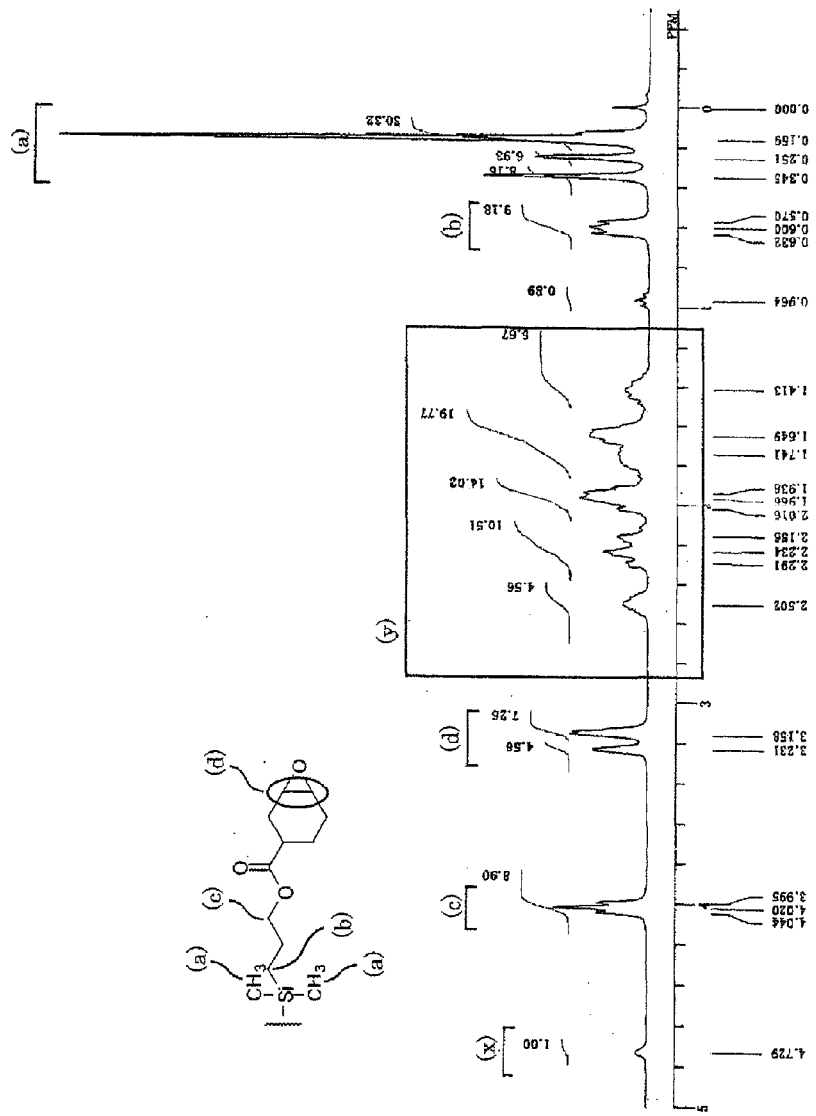
FIG. 5 is a $^1$H-NMR spectrum of the product obtained in Example 3.
Figure 6:
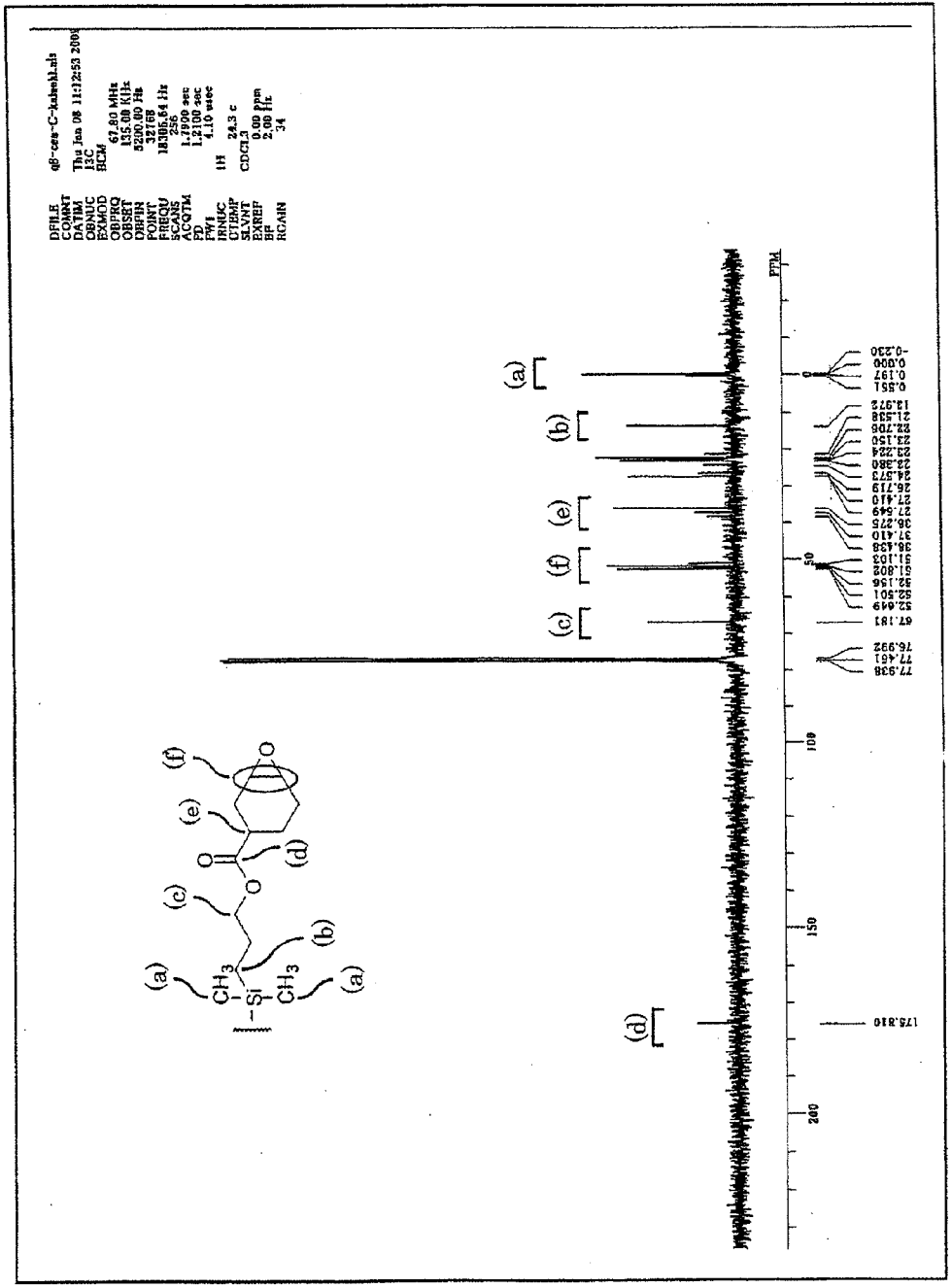
FIG. 6 is a $^{13}$C-NMR spectrum of the product obtained in Example 3.
Figure 7:
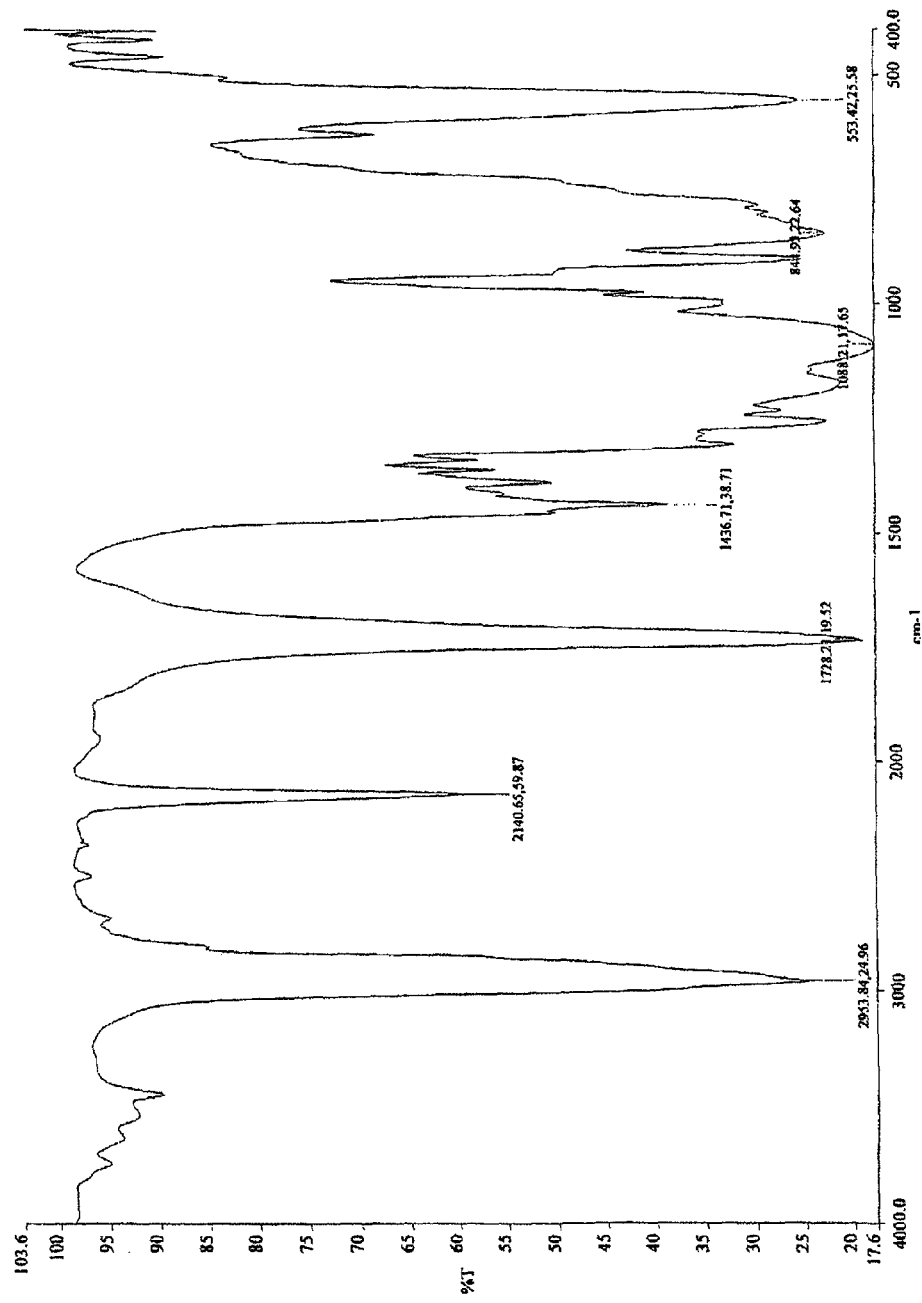
FIG. 7 is an IR spectrum of the product obtained in Example 3.

A $^1$H-NMR spectrum, a $^{13}$C-NMR spectrum and an IR spectrum of the nonvolatile component thus obtained are shown respectively in FIG. 5, FIG. 6 and FIG. 7. In FIG. 5, peaks marked with (a) to (d) are peaks corresponding respectively to parts shown by (a) to (d) marked on the structural formulas. The same shall apply as well to FIG. 6 and the subsequent figures. Also, in FIG. 5, a peak marked with (x) is a peak corresponding to H of an unreacted Si—H group, and peaks marked with (y) are peaks corresponding to H of groups other than the above group.

It can be found from FIG. 5 that a peak of the unreacted Si—H group is present in 4.73 ppm and that comparison of the above peak with a peak of 2H in a methylene part adjacent to an oxygen atom of a reaction part which is present in about 4 ppm shows (the number of the unreacted part (Si—H)):(the number of the reacted part)=1.45:6.55 based on the eight reaction parts.

In FIG. 6, observed as peaks characteristic to the nonvolatile component obtained were a peak of carbon of a carbonyl group in the vicinity of 175.8 ppm, a peak of carbon of methylene adjacent to an oxygen atom in the vicinity of 67.2 ppm, a peak of carbon adjacent to oxygen of an epoxy group in the vicinity of 50 ppm, a peak of carbon of methylene adjacent to a silicon atom in the vicinity of 14.0 ppm and a peak of carbon of methyl adjacent to a silicon atom in the vicinity of 0 ppm.

Also, in an IR spectrum of FIG. 7, a peak of a Si—H group was observed in 2140 cm$^{-1}$. Further, a peak of a carbonyl group was observed in 1728 cm$^{-1}$.

It was found from the above results that the nonvolatile component obtained was a mixture of epoxy compounds in which 1 to 8 groups out of 8 groups of A in the epoxy compound (hereinafter referred to as the epoxy compound (V)) represented by Formula (V) shown below were reacted:

[Ka 26]

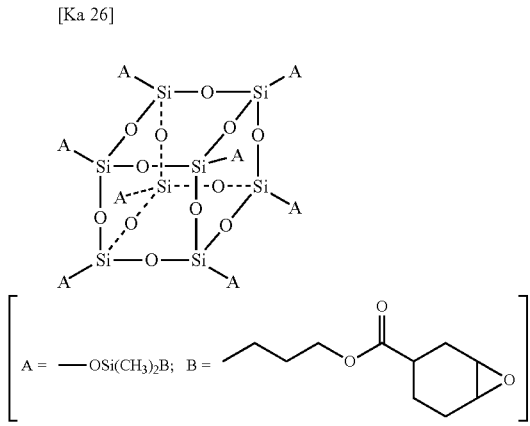

(V)

Example 4

A three neck flask of 100 ml equipped with a reflux condenser, a thermometer, a stirring device and a serum cap was charged with 0.897 g (5.88 mmol) of limonene oxide and 0.00093 g (0.02 mol %) of a 2% divinyltetramethyldisiloxane platinum complex xylene solution, and the mixture was stirred at 110° C. under argon flow. Then, 1.0 g (0.98 mmol) of PSS-octakis(dimethylsilyloxy) substituted dissolved in 5.0 ml of toluene was slowly added thereto by means of a dropping funnel. Stirring was continued for 12 hours while maintaining the above temperature, and after confirming by gas chromatography that a whole amount of limonene oxide was consumed, the reaction was finished. The toluene solvent was removed under reduced pressure to obtain an epoxy compound represented by Formula (VII) shown below (hereinafter referred to as the epoxy compound (VII)) as a nonvolatile component.

Figure 8:
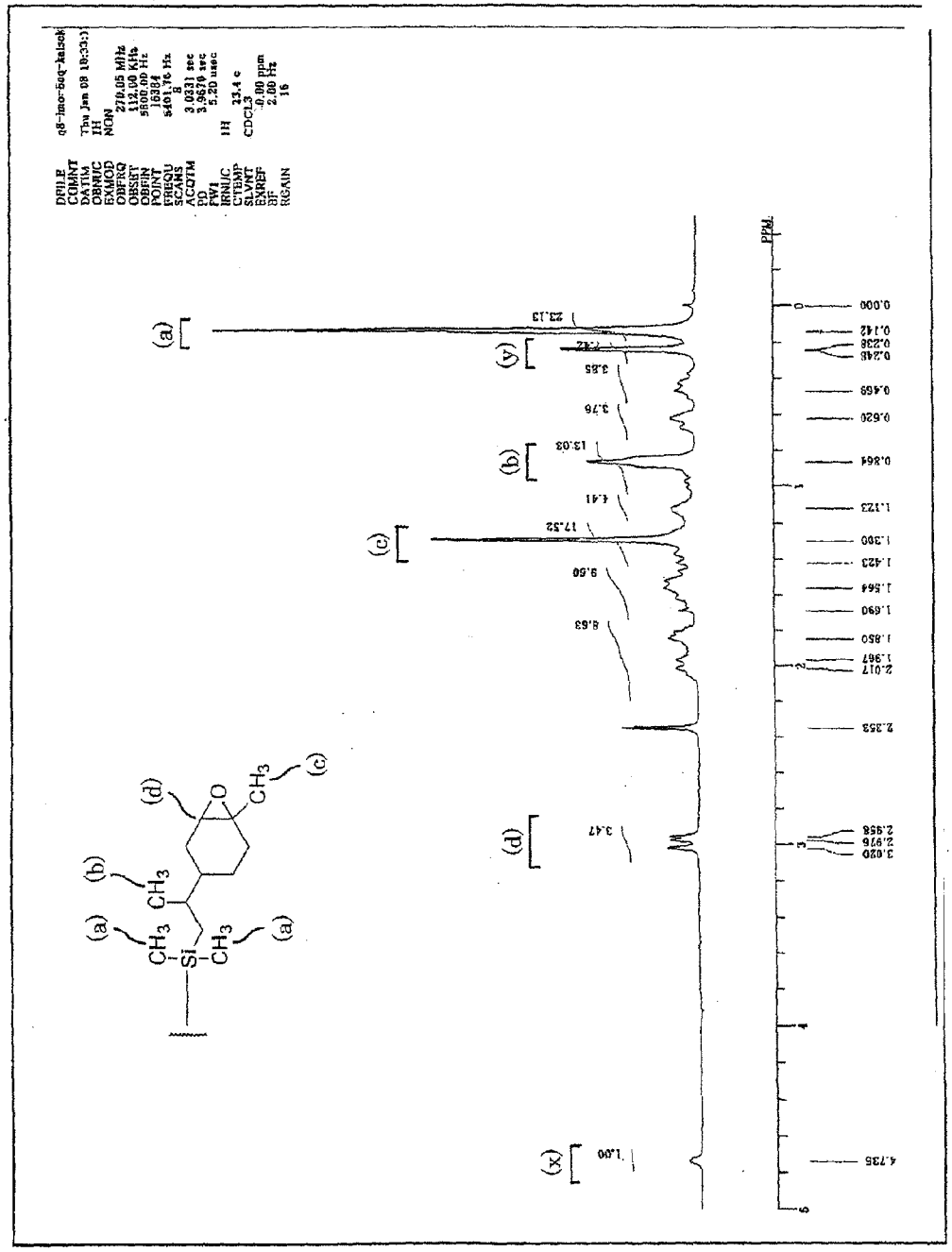
FIG. 8 is a $^1$H-NMR spectrum of the product obtained in Example 4.
Figure 9:
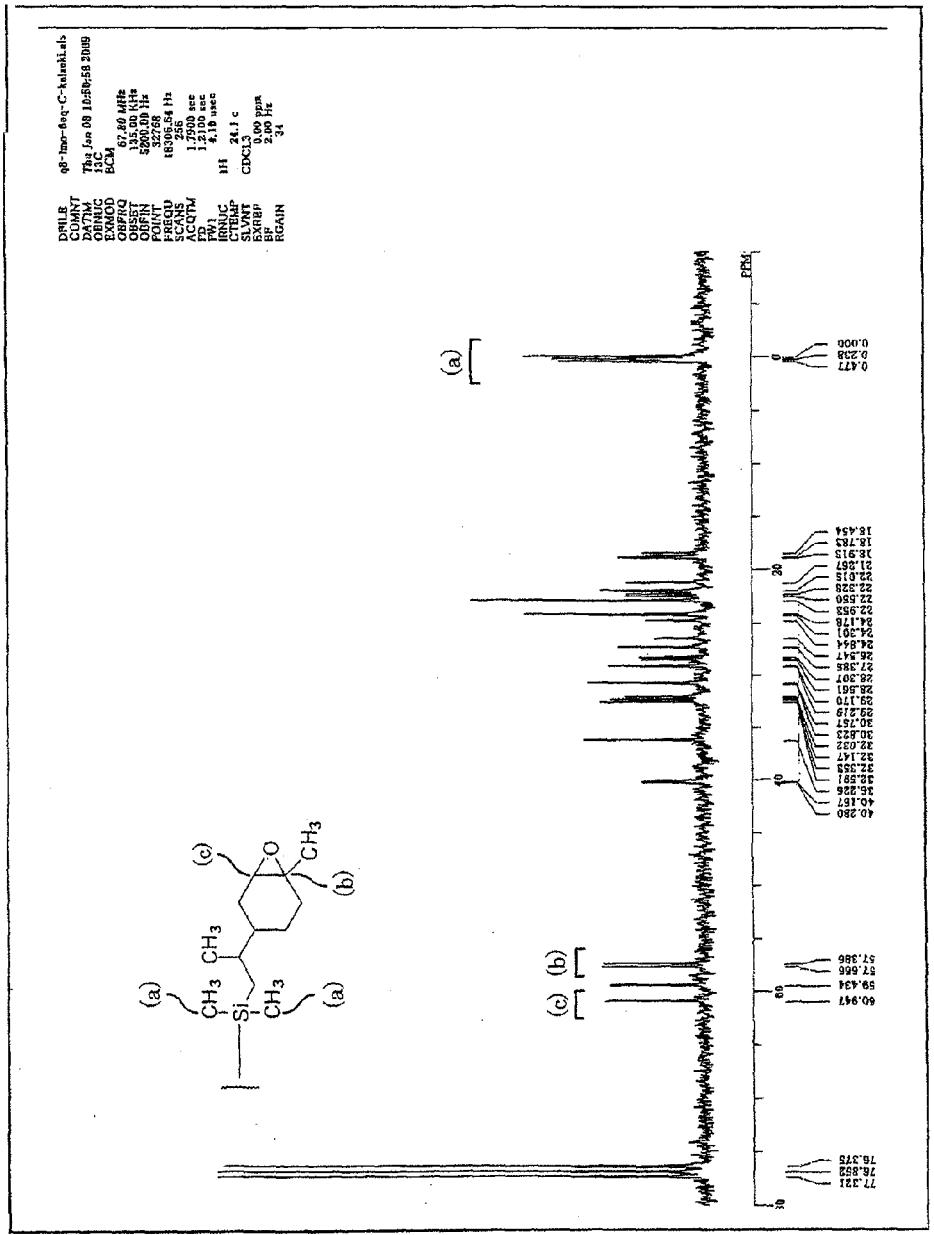
FIG. 9 is a $^{13}$C-NMR spectrum of the product obtained in Example 4.
Figure 10:
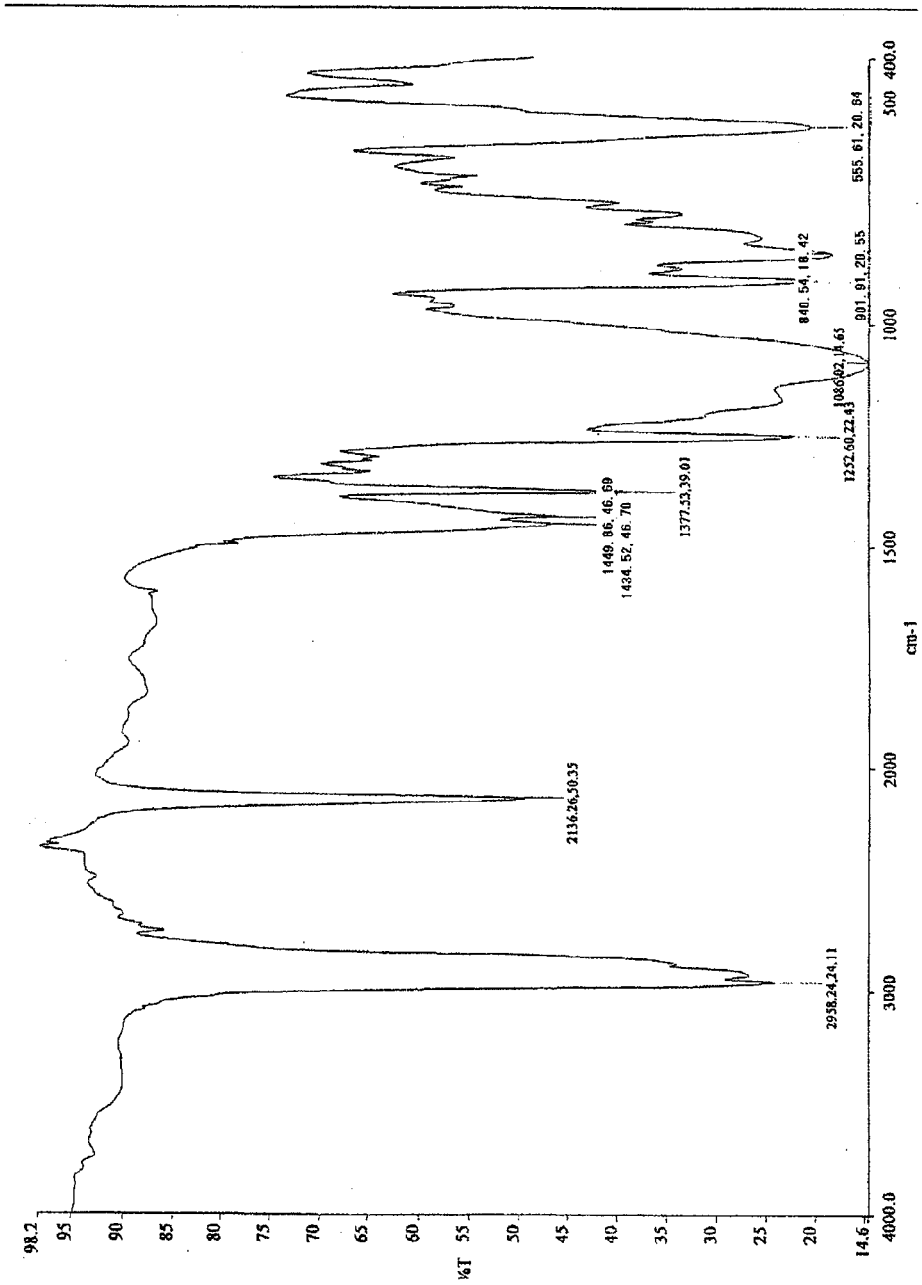
FIG. 10 is an IR spectrum of the product obtained in Example 4.

A $^1$H-NMR spectrum, a $^{13}$C-NMR spectrum and an IR spectrum of the nonvolatile component thus obtained are shown respectively in FIG. 8, FIG. 9 and FIG. 10. In FIG. 8, a peak marked with (x) is a peak corresponding to H of an unreacted Si—H group, and a peak marked with (y) is a peak corresponding to H of two CH$_3$ bonded to Si of an unreacted Si—H group.

It can be found from FIG. 8 that a peak of an unreacted Si—H group is present in 4.74 ppm and that comparison of the above peak with a peak of 1H on carbon adjacent to an oxygen atom of an epoxy group which is present in about 3 ppm shows (the number of the unreacted part (Si—H)):(the number of the reacted part)=2:6 based on the eight reaction parts, and the above result agrees with the charge ratio in the reaction.

In FIG. 9, observed as peaks characteristic to the nonvolatile component obtained were a peak of carbon adjacent to an oxygen atom of an epoxy group in the vicinity of 60.9 ppm, a peak of carbon which is adjacent to an oxygen atom of an epoxy group and which has methyl in the vicinity of 57 ppm and a peak of carbon of methyl adjacent to a silicon atom in the vicinity of 0 ppm.

Also, in an IR spectrum of FIG. 10, a peak of a Si—H group was observed in 2156 cm$^{-1}$.

It was found from the above results that the nonvolatile component obtained was an epoxy compound in which 6 groups out of 8 groups of J in the epoxy compound (hereinafter referred to as the epoxy compound (VII)) represented by Formula (VII) shown below were reacted:

[Ka 27]

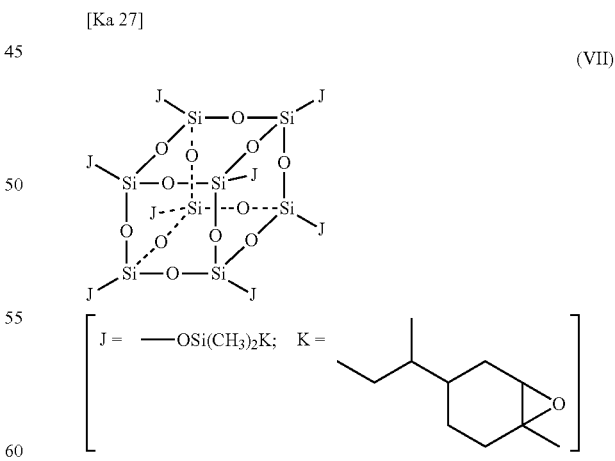

(VII)

Example 5

A three neck flask of 100 ml equipped with a reflux condenser, a thermometer, a stirring device and a serum cap was charged with 0.598 g (3.92 mmol) of limonene oxide and 0.00093 g (0.02 mol %) of a 2% divinyltetramethyldisiloxane platinum complex xylene solution, and the mixture was stirred at 110° C. under argon flow. Then, 1.0 g (0.98 mmol) of PSS-octakis(dimethylsilyloxy) substituted dissolved in 5.0 ml of toluene was slowly added thereto by means of a dropping funnel. Stirring was continued for 12 hours while maintaining the above temperature, and after confirming by gas chromatography that a whole amount of limonene oxide was consumed, the reaction was finished. The toluene solvent was removed under reduced pressure to obtain the epoxy compound represented by Formula (VII) shown below (hereinafter referred to as the epoxy compound (VII)) as a nonvolatile component.

Figure 11:
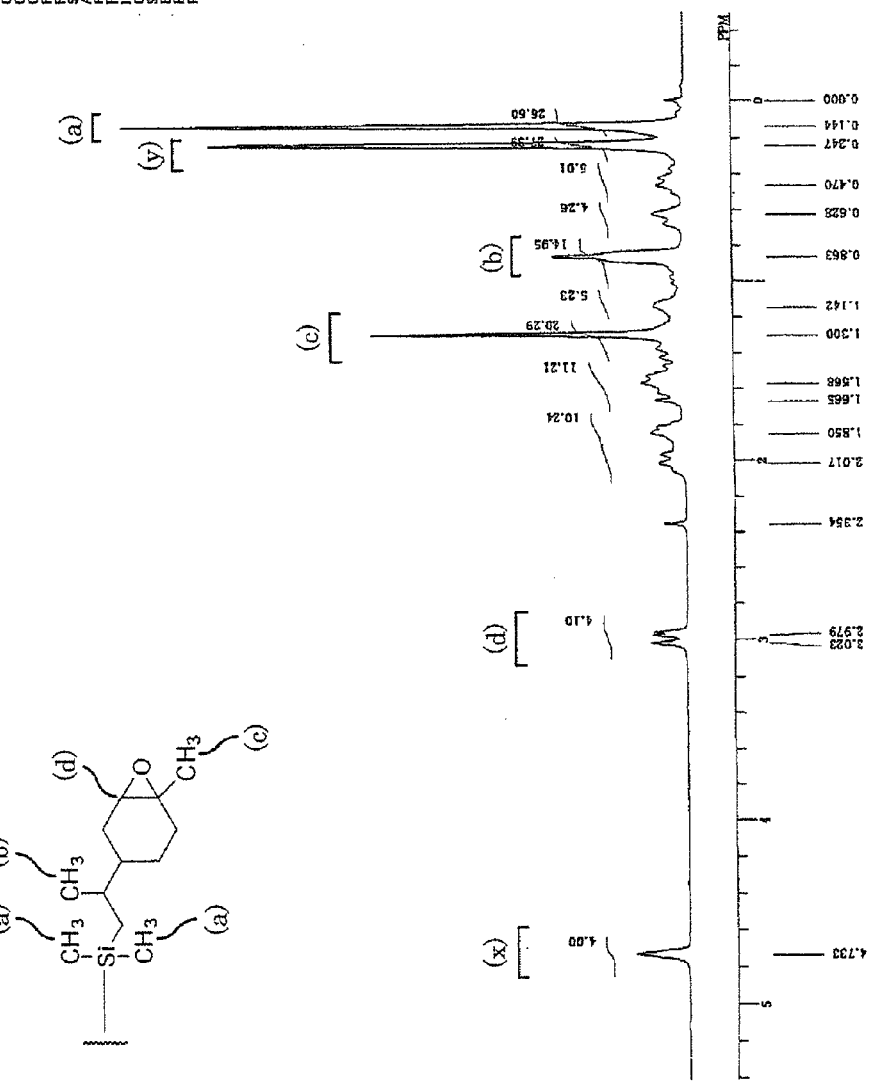
FIG. 11 is a $^1$H-NMR spectrum of the product obtained in Example 5.
Figure 12:
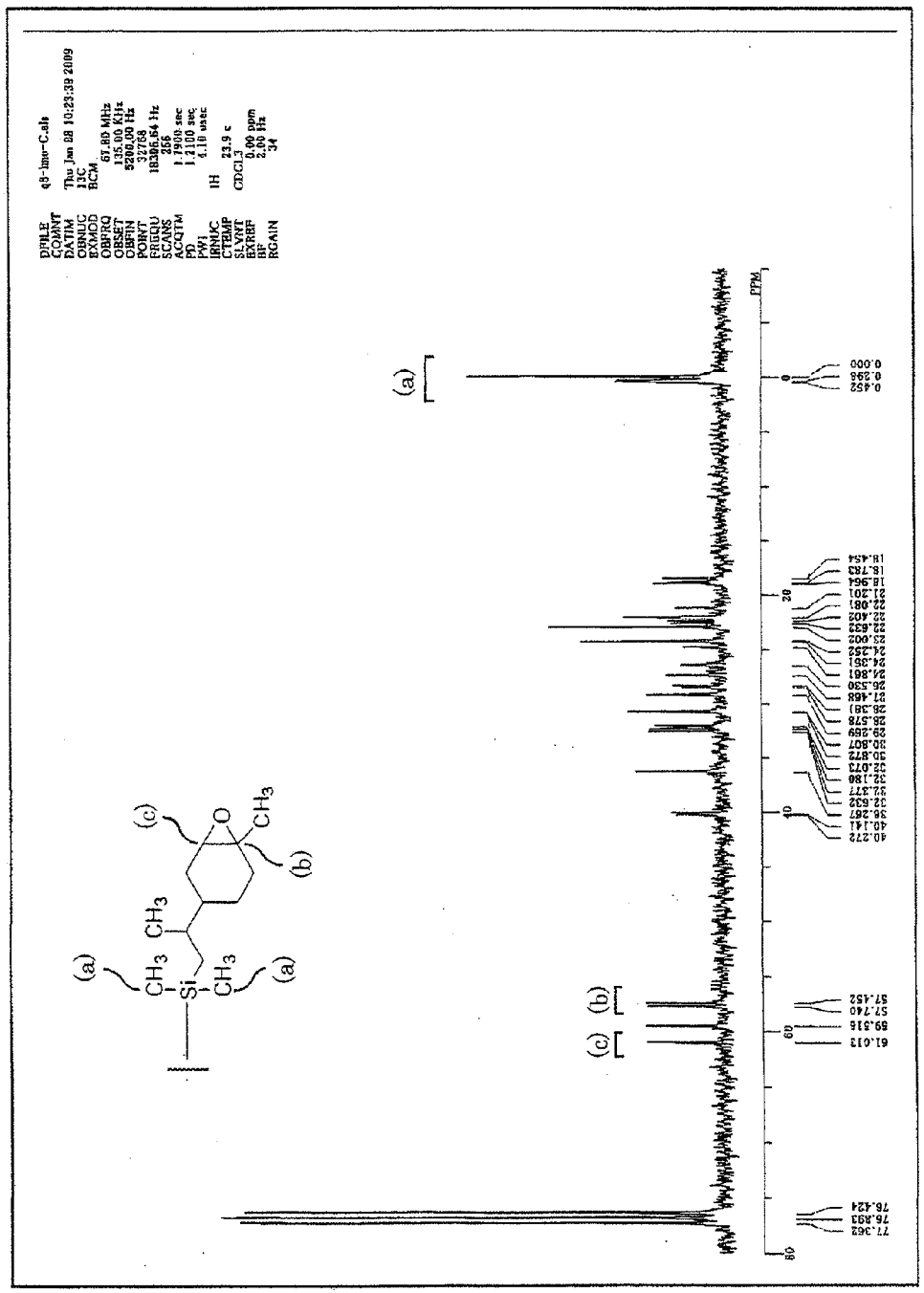
FIG. 12 is a $^{13}$C-NMR spectrum of the product obtained in Example 5.
Figure 13:
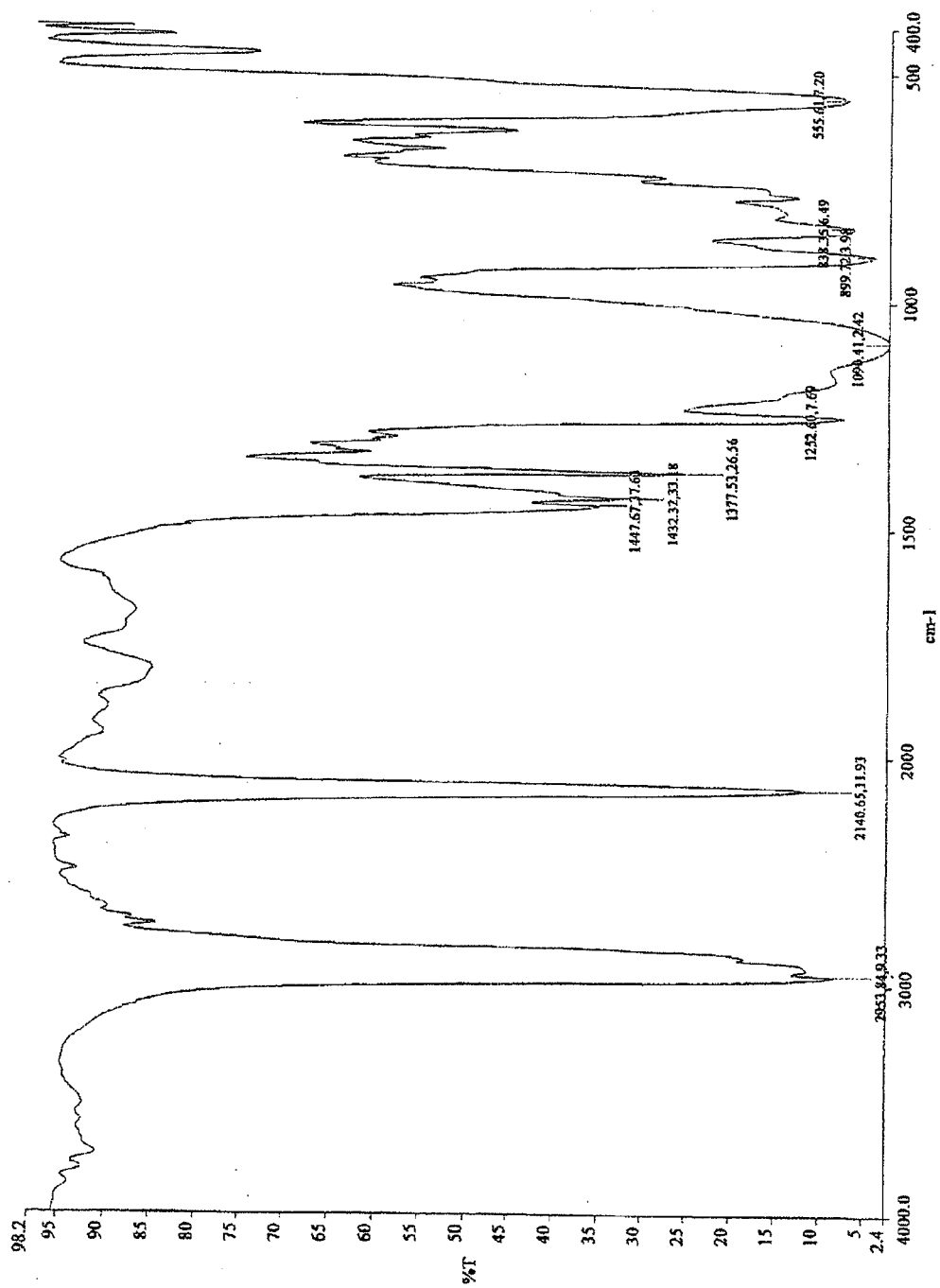
FIG. 13 is an IR spectrum of the product obtained in Example 5.

A $^1$H-NMR spectrum, a $^{13}$C-NMR spectrum and an IR spectrum of the nonvolatile component thus obtained are shown respectively in FIG. 11, FIG. 12 and FIG. 13. In FIG. 11, a peak marked with (x) is a peak corresponding to H of an unreacted Si—H group, and a peak marked with (y) is a peak corresponding to H of two CH$_3$ bonded to Si of an unreacted Si—H group.

It can be found from FIG. 11 that a peak of an unreacted Si—H group is present in 4.73 ppm and that comparison of the above peak with a peak of 1H on carbon adjacent to an oxygen atom of an epoxy group which is present in about 3 ppm shows (the number of the unreacted part (Si—H)):(the number of the reacted part)=4:4 based on the eight reaction parts, and the above result agrees with the charge ratio in the reaction.

In FIG. 12, observed as peaks characteristic to the nonvolatile component obtained were a peak of carbon adjacent to an oxygen atom of an epoxy group in the vicinity of 61.0 ppm, a peak of carbon which is adjacent to an oxygen atom of an epoxy group and which has methyl in the vicinity of 57 ppm and a peak of carbon of methyl adjacent to a silicon atom in the vicinity of 0 ppm.

Also, in an IR spectrum of FIG. 10, a peak of a Si—H group was observed in 2140 cm$^{-1}$.

It was found from the above results that the nonvolatile component obtained was an epoxy compound in which 4 groups out of 8 groups of J in the epoxy compound (hereinafter referred to as the epoxy compound (VII)) represented by Formula (VII) shown below were reacted:

[Ka 28]

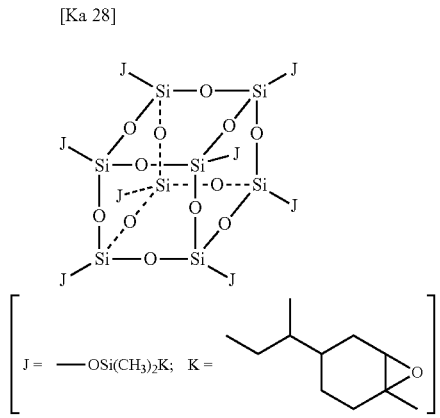

(VII)

Example 6

A three neck flask of 100 ml equipped with a reflux condenser, a thermometer, a stirring device and a serum cap was charged with 1.196 g (7.84 mmol) of limonene oxide and 0.00093 g (0.02 mol %) of a 2% divinyltetramethyldisiloxane platinum complex xylene solution, and the mixture was stirred at 110° C. under argon flow. Then, 1.0 g (0.98 mmol) of PSS-octakis(dimethylsilyloxy) substituted dissolved in 5.0 ml of toluene was slowly added thereto by means of a dropping funnel (a —SiH group contained in PSS-octakis(dimethylsilyloxy) substituted corresponds to 1 equivalent based on 1 equivalent of an ethylenical double bond contained in limonene oxide). Stirring was continued for 12 hours while maintaining the above temperature, and after confirming by gas chromatography that a whole amount of limonene oxide was consumed, the reaction was finished. The toluene solvent was removed under reduced pressure to obtain the epoxy compound represented by Formula (VII) shown below (hereinafter referred to as the epoxy compound (VII)) as a nonvolatile component.

Figure 14:
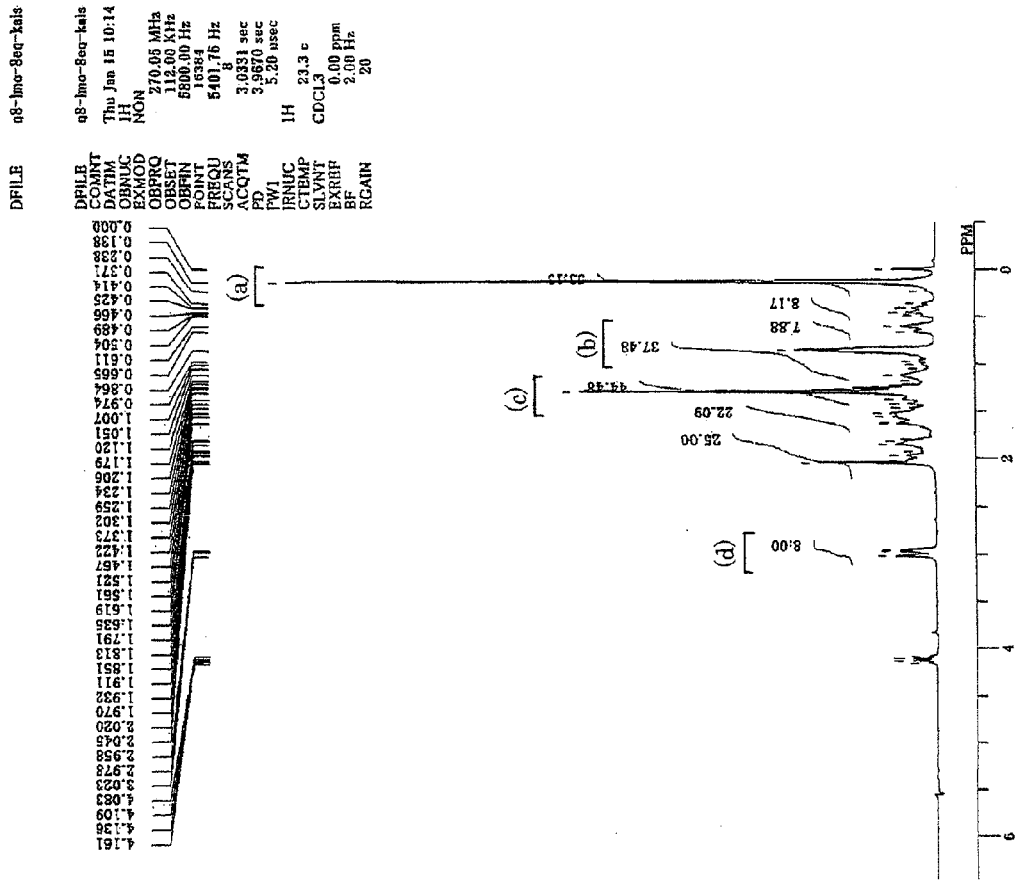
FIG. 14 is a $^1$H-NMR spectrum of the product obtained in Example 6.
Figure 15:
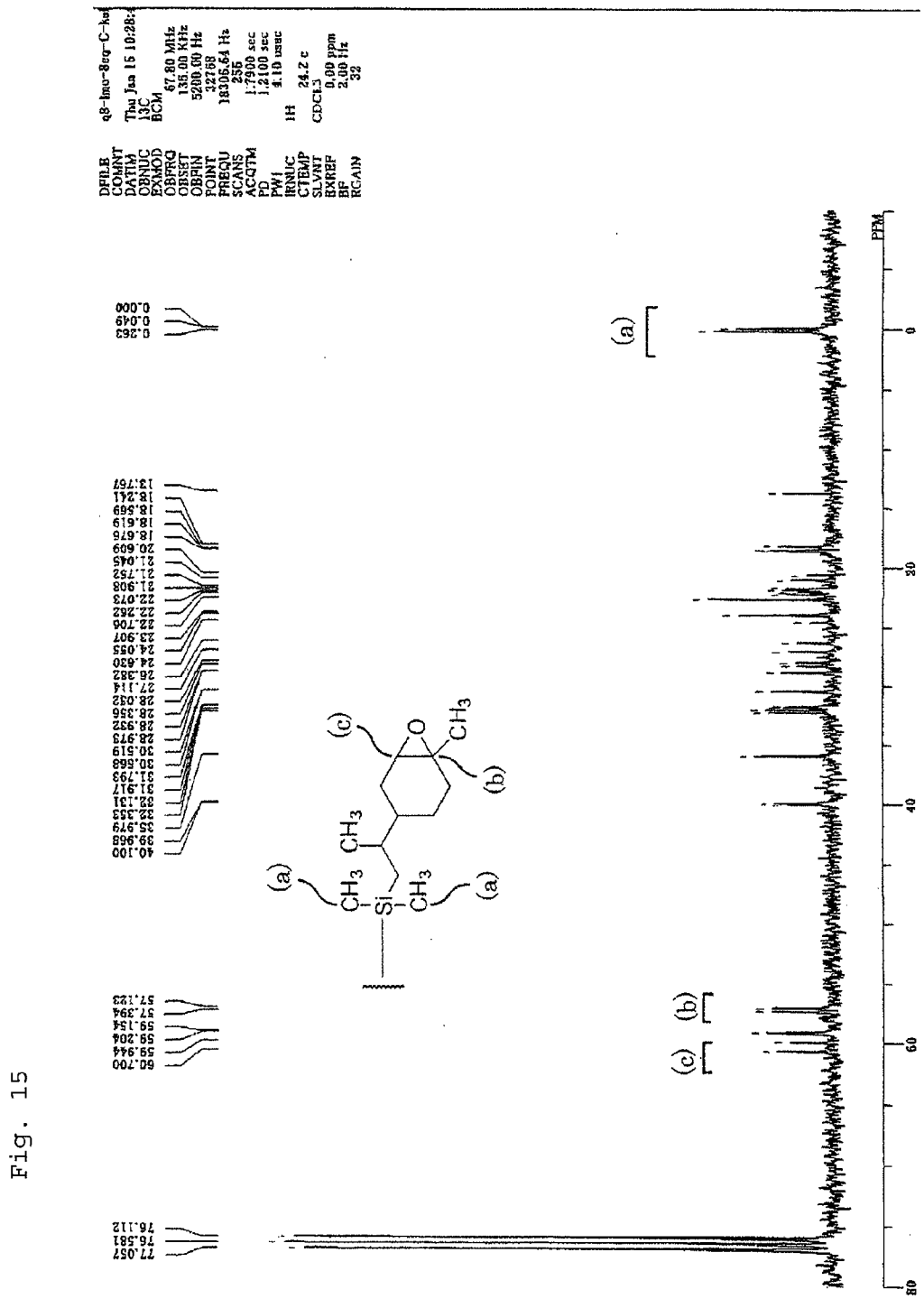
FIG. 15 is a $^{13}$C-NMR spectrum of the product obtained in Example 6.
Figure 16:
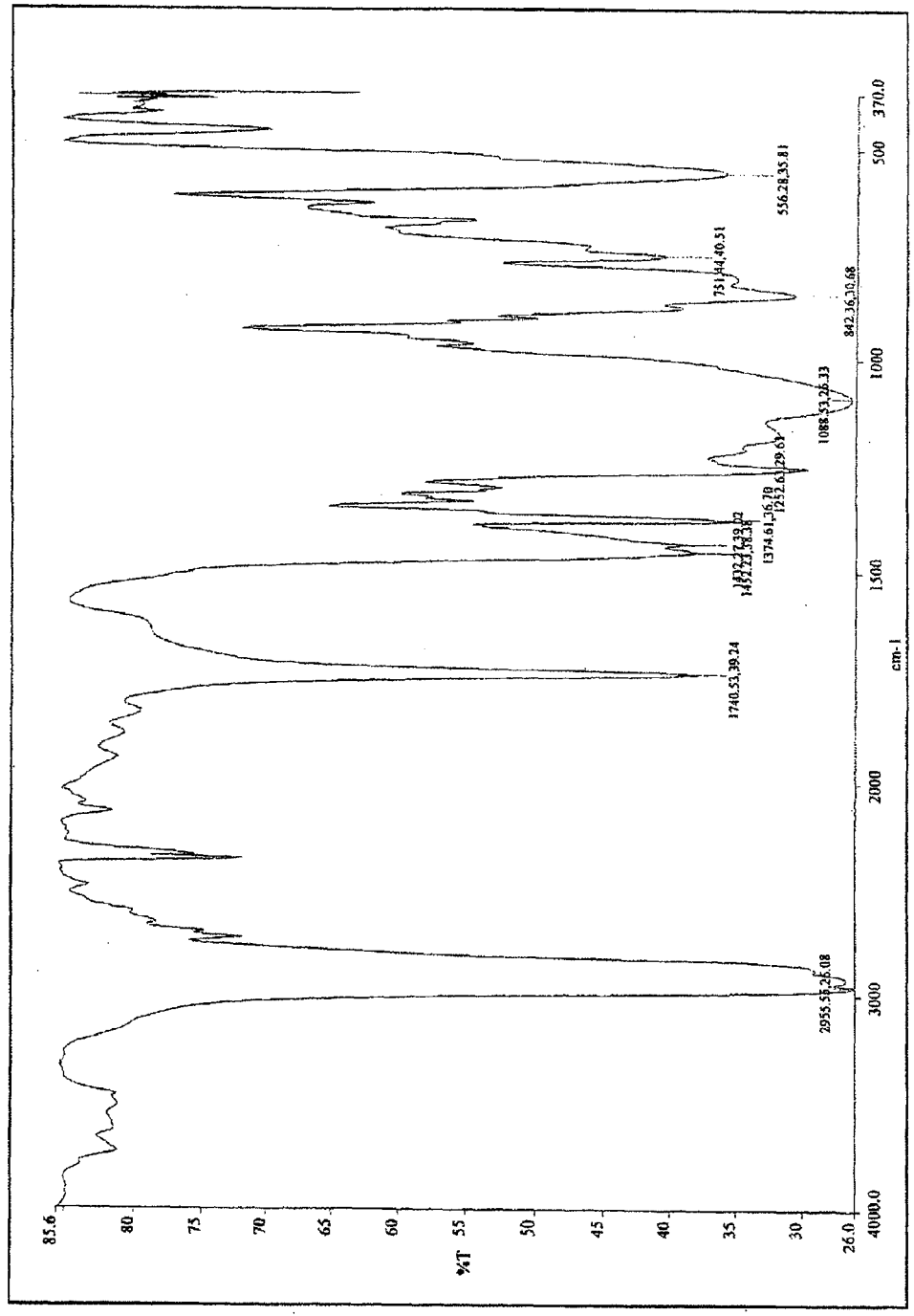
FIG. 16 is an IR spectrum of the product obtained in Example 6.

A $^1$H-NMR spectrum, a $^{13}$C-NMR spectrum and an IR spectrum of the nonvolatile component thus obtained are shown respectively in FIG. 14, FIG. 15 and FIG. 16.

In FIG. 14, a peak corresponding to an unreacted Si—H group was not observed in the vicinity of 4.7 ppm.

In FIG. 15, observed as peaks characteristic to the nonvolatile component obtained were a peak of carbon adjacent to an oxygen atom of an epoxy group in the vicinity of 61.0 ppm, a peak of carbon which is adjacent to an oxygen atom of an epoxy group and which has methyl in the vicinity of 57 ppm and a peak of carbon of methyl adjacent to a silicon atom in the vicinity of 0 ppm.

Also, in an IR spectrum of FIG. 16, a peak assigned to a Si—H group was not observed. Further, it was confirmed from GC analysis that limonene oxide which was the raw material was completely consumed.

It was found from the above results that the nonvolatile component obtained was an epoxy compound in which all 8 groups of J in the epoxy compound (hereinafter referred to as the epoxy compound (VII)) represented by Formula (VII) shown below were reacted:

[Ka 29]

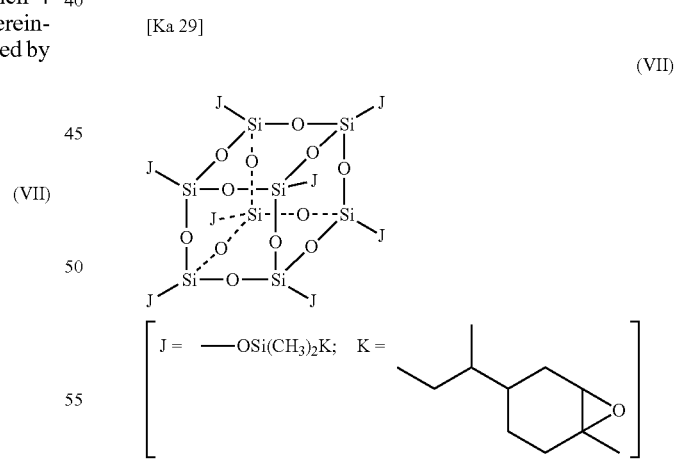

(VII)

The invention claimed is:

1. An epoxy compound represented by Formula (I):

$$YSiO_{3/2})_n \qquad (I)$$

(in Formula (I), p (p is a natural number equal to n or less) groups of Y out of n groups thereof represent groups represented by any of Formulas (2a) to (5a) shown below, and (n–p) groups of Y represent a hydrogen atom or —OSiR$^1_2$H; n represents an integer of 2 to 500; R$^1$ represents independently an alkyl group having 1 to 5 carbon atoms):

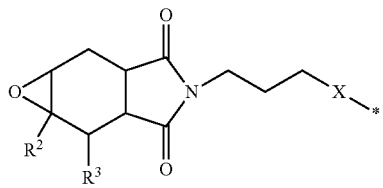
(2a)

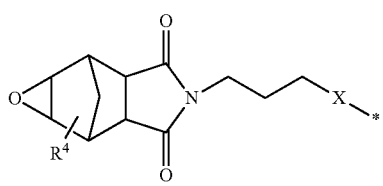
(3a)

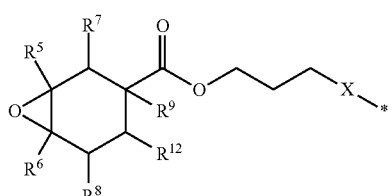
(4a)

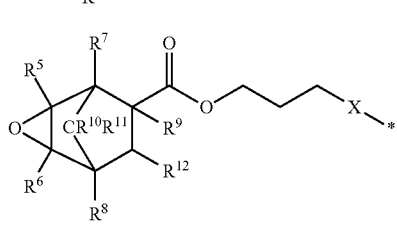
(5a)

(in Formulas (2a) to (5a), R$^2$ and R$^3$ each represent independently a hydrogen atom, an alkyl group having 1 to 6 carbon atoms or a trialkylsilyl group having 3-12 carbon atoms;

R$^4$ represents a hydrogen atom, an alkyl group having 1 to 6 carbon atoms or a trialkylsilyl group having 3-12 carbon atoms; R$^5$ to R$^{11}$ each represent independently a hydrogen atom, an alkyl group having 1 to 6 carbon atoms or a trialkylsilyl group having 3-12 carbon atoms;

R$^{12}$ represents a hydrogen atom, an alkyl group having 1 to 6 carbon atoms, a trialkylsilyl group having 3-12 carbon atoms or an aryl group;

\* represents a bonding part with Si shown in Formula (I), and —X—\* represents —\* in which X is a single bond or a group represented by Formula (x) shown below):

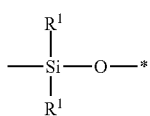
(x)

(in Formula (x), R$^1$ represents an alkyl group having 1 to 5 carbon atoms).

2. The epoxy compound as described in claim 1, wherein the epoxy compound has a cage-like silsesquioxane structure or a ladder-like silsesquioxane structure.

3. The epoxy compound as described in claim 2, wherein in Formulas (2a) to (5a), —X—\* is the group represented by Formula (x), and in Formula (x), R$^1$ is methyl or ethyl.

4. The epoxy compound as described in claim 1, wherein in Formulas (2a) to (5a), R$^2$ to R$^{11}$ each are independently a hydrogen atom or methyl, and R$^{12}$ is a hydrogen atom, methyl or phenyl.

5. The epoxy compound as described in claim 1, wherein the compound is liquid at 10 to 30° C.

6. A production process for the epoxy compound as described in claim 1, comprising the step of:
reacting a compound represented by Formula (III) or (IV):

$$(Y^1SiO_{3/2})_n \qquad (III)$$

(in Formula (III), Y$^1$ represents a hydrogen atom or —OSiR$^1_2$H; R$^1$ represents an alkyl group having 1 to 5 carbon atoms; and n represents an integer of 2 to 500);

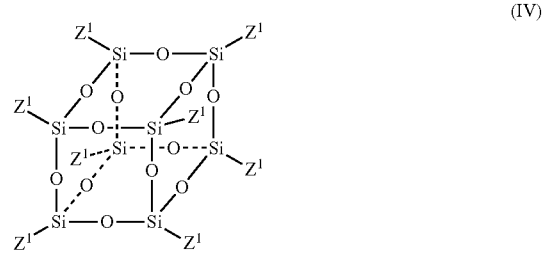
(IV)

(in Formula (IV), Z$^1$ represents —OSiR$^1_2$H, and R$^1$ represents an alkyl group having 1 to 5 carbon atoms) with an epoxy compound represented by any of Formulas (6) to (10) shown below:

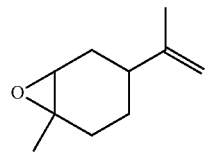
(6)

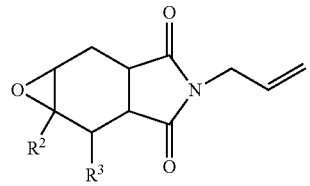
(7)

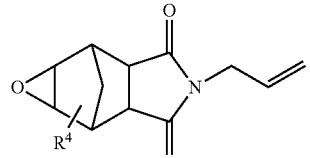
(8)

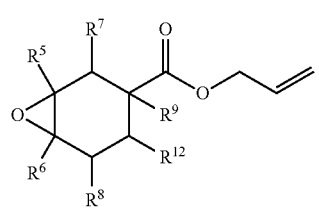
(9)

-continued

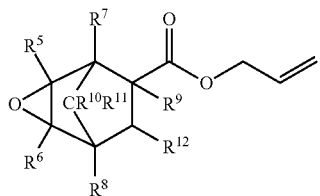
(10)

(in Formulas (7) to (10), $R^2$ and $R^3$ each represent independently a hydrogen atom, an alkyl group having 1 to 6 carbon atoms or a trialkylsilyl group having 3-12 carbon atoms; $R^4$ represents a hydrogen atom, an alkyl group having 1 to 6 carbon atoms or a trialkylsilyl group having 3-12 carbon atoms; $R^5$ to $R^{11}$ each represent independently a hydrogen atom, an alkyl group having 1 to 6 carbon atoms or a trialkylsilyl group having 3-12 carbon atoms; $R^{12}$ represents a hydrogen atom, an alkyl group having 1 to 6 carbon atoms, a trialkylsilyl group having 3-12 carbon atoms or an aryl group) at 10 to 200° C.

7. The production process for the epoxy compound as described in claim 6, wherein the compound represented by Formula (III) or (IV) is represented by Formula (III), and has a cage-like silsesquioxane structure or a ladder-like silsesquioxane structure.

8. The production process for the epoxy compound as described in claim 7, wherein in Formulas (7) to (10), $R^2$ to $R^{11}$ each are independently a hydrogen atom or methyl, and $R^{12}$ is a hydrogen atom, methyl or phenyl.

9. The production process for the epoxy compound as described in claim 6, wherein the compound represented by Formula (III) or (IV) is represented by Formula (IV), and in Formula (IV) $R^1$ is methyl or ethyl.

10. The production process for the epoxy compound as described in claim 9, wherein in Formulas (7) to (10), $R^2$ to $R^{11}$ each are independently a hydrogen atom or methyl, and $R^{12}$ is a hydrogen atom, methyl or phenyl.

11. The production process for the epoxy compound as described in claim 6, wherein in Formulas (7) to (10), $R^2$ to $R^{11}$ each are independently a hydrogen atom or methyl, and $R^{12}$ is a hydrogen atom, methyl or phenyl.

12. The production process for the epoxy compound as described in claim 6, wherein the epoxy compound and the compound represented by Formula (III) or (IV) are blended so that an equivalent of a —SiH group contained in the compound represented by Formula (III) or (IV) is 0.3 to 1.5 based on 1 equivalent of an ethylenic double bond contained in the epoxy compound.

13. The production process for the epoxy compound according to claim 6, wherein the compound of Formula (III) or (IV) is reacted with an epoxy compound represented by any of Formulas (7) to (10).

14. An epoxy compound represented by Formula (I):

$$(YSiO_{3/2})_n \quad (I)$$

(in Formula (I), p (p is a natural number equal to n or less) groups of Y out of n groups thereof represent groups represented by any of Formulas (1a) to (5a) shown below, and (n–p) groups of Y represent a hydrogen atom or —OSiR$^1_2$H; n represents an integer of 2 to 500; $R^1$ represents independently an alkyl group having 1 to 5 carbon atoms):

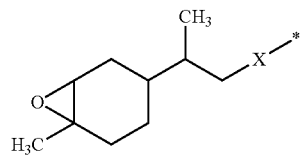
(1a)

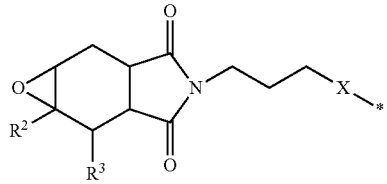
(2a)

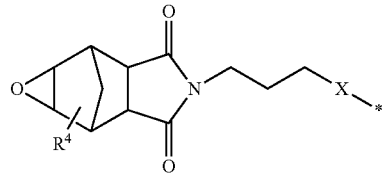
(3a)

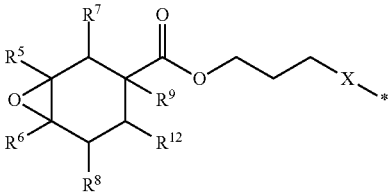
(4a)

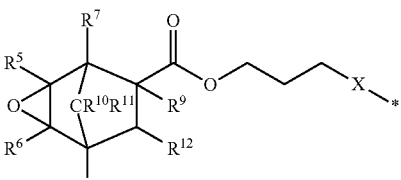
(5a)

(in Formulas (1a) to (5a), $R^2$ and $R^3$ each represent independently a hydrogen atom, an alkyl group having 1 to 6 carbon atoms or a trialkylsilyl group having 3-12 carbon atoms; $R^4$ represents a hydrogen atom, an alkyl group having 1 to 6 carbon atoms or a trialkylsilyl group having 3-12 carbon atoms; $R^5$ to $R^{11}$ each represent independently a hydrogen atom, an alkyl group having 1 to 6 carbon atoms or a trialkylsilyl group having 3-12 carbon atoms; $R^{12}$ represents a hydrogen atom, an alkyl group having 1 to 6 carbon atoms, a trialkylsilyl group having 3-12 carbon atoms or any aryl group;

* represents a bonding part with Si shown in Formula (I), and —X—* represents a group represented by Formula (x) shown below):

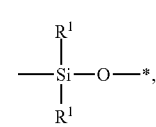
(x)

wherein in Formula (x), $R^1$ is methyl or ethyl.

15. The epoxy compound as described in claim 14, wherein in Formulas (2a) to (5a), $R^2$ to $R^{11}$ each are independently a hydrogen atom or methyl, and $R^{12}$ is a hydrogen atom, methyl or phenyl.

16. The epoxy compound according to claim 14, wherein the compound represented by Formula (I) has a Y group that is represented by any of Formulas (2a) to (5a).

17. An epoxy compound represented by Formula (II):

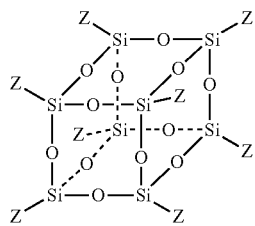

(II)

(in Formula (II), q (q is a natural number equal to 8 or less) groups out of eight Z represent —OSiR$^1_2$Y$^1$, and (8−q) groups of Z represent a hydrogen atom or —OSiR$^1_2$H; R$^1$ represents an alkyl group having 1 to 5 carbon atoms; and Y$^1$ represents a group represented by any of Formulas (1b) to (5b) shown below):

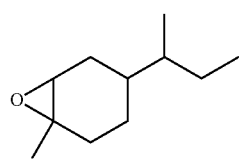

(1b)

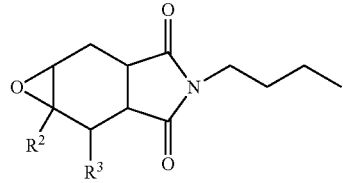

(2b)

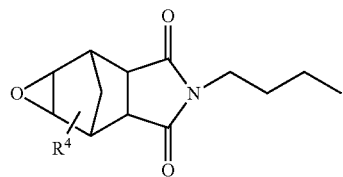

(3b)

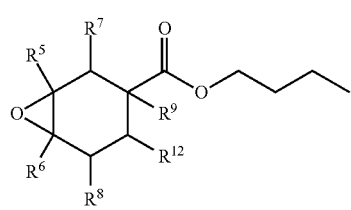

(4b)

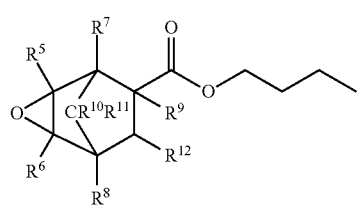

(5b)

(in Formulas (1b) to (5b), R$^2$ and R$^3$ each represent independently a hydrogen atom, an alkyl group having 1 to 6 carbon atoms or a trialkylsilyl group having 3-12 carbon atoms;

R$^4$ represents a hydrogen atom, an alkyl group having 1 to 6 carbon atoms or a trialkylsilyl group having 3-12 carbon atoms; R$^5$ to R$^{11}$ each represent independently a hydrogen atom, an alkyl group having 1 to 6 carbon atoms or a trialkylsilyl group having 3-12 carbon atoms;

R$^{12}$ represents a hydrogen atom, an alkyl group having 1 to 6 carbon atoms, a trialkylsilyl group having 3-12 carbon atoms or an aryl group).

18. The epoxy compound as described in claim 17, wherein in Formula (II), R$^1$ is methyl or ethyl.

19. The epoxy compound as described in claim 18, wherein in Formulas (2b) to (5b), R$^2$ to R$^{11}$ each are independently a hydrogen atom or methyl, and R$^{12}$ is a hydrogen atom, methyl or phenyl.

20. The epoxy compound as described in claim 17, wherein in Formulas (2b) to (5b), R$^2$ to R$^{11}$ each are independently a hydrogen atom or methyl, and R$^{12}$ is a hydrogen atom, methyl or phenyl.

21. The epoxy compound as described in claim 17, wherein the compound is liquid at 10 to 30° C.

22. The epoxy compound according to claim 17, wherein the compound represented by Formula (II) has a Y$^1$ group that is represented by any of Formulas (2b) to (5b).

23. An epoxy compound obtained by blending a compound represented by Formula (IV):

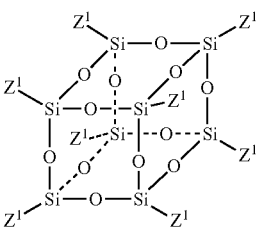

(IV)

(in Formula (IV), Z$^1$ represents —OSiR$^1_2$H, and R$^1$ represents an alkyl group having 1 to 5 carbon atoms) with an epoxy compound represented by any of Formulas (6) to (10) shown below:

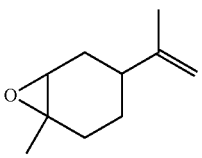

(6)

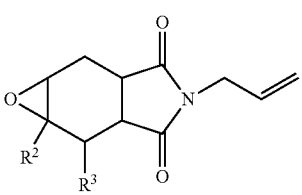

(7)

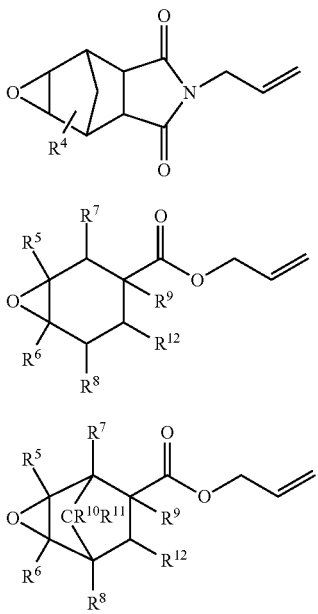

(in Formulas (7) to (10), $R^2$ and $R^3$ each represent independently a hydrogen atom, an alkyl group having 1 to 6 carbon atoms or a trialkylsilyl group having 3-12 carbon atoms;

$R^4$ represents a hydrogen atom, an alkyl group having 1 to 6 carbon atoms or a trialkylsilyl group having 3-12 carbon atoms; $R^5$ to $R^{11}$ each represent independently a hydrogen atom, an alkyl group having 1 to 6 carbon atoms or a trialkylsilyl group having 3-12 carbon atoms;

$R^{12}$ represents a hydrogen atom, an alkyl group having 1 to 6 carbon atoms, a trialkylsilyl group having 3-12 carbon atoms or an aryl group) so that an equivalent of a —SiH group contained in the compound represented by Formula (IV) is 0.3 to 1.5 based on 1 equivalent of an ethylenic double bond contained in the epoxy compound and subjecting them to hydrosilylation reaction at 10 to 200° C.

24. The epoxy compound as described in claim 23, wherein $R^1$ of the compound represented by Formula (IV) is methyl, and the epoxy compound is represented by Formula (6) or (9).

25. The epoxy compound according to claim 23, wherein the compound represented by Formula (IV) is blended with an epoxy compound represented by any of Formulas (7) to (10).

* * * * *